US010952658B2

(12) United States Patent
Yamaoka et al.

(10) Patent No.: US 10,952,658 B2
(45) Date of Patent: Mar. 23, 2021

(54) INFORMATION PROCESSING METHOD, INFORMATION PROCESSING DEVICE, AND INFORMATION PROCESSING SYSTEM

(71) Applicant: PANASONIC INTELLECTUAL PROPERTY CORPORATION OF AMERICA, Torrance, CA (US)

(72) Inventors: Masaru Yamaoka, Osaka (JP); Mikiko Matsuo, Nara (JP)

(73) Assignee: PANASONIC INTELLECTUAL PROPERTY CORPORATION OF AMERICA, Torrance, CA (US)

( * ) Notice: Subject to any disclaimer, the term of this patent is extended or adjusted under 35 U.S.C. 154(b) by 121 days.

(21) Appl. No.: 16/284,506

(22) Filed: Feb. 25, 2019

(65) Prior Publication Data

US 2019/0298241 A1   Oct. 3, 2019

(30) Foreign Application Priority Data

Apr. 3, 2018   (JP) .............................. JP2018-071841

(51) Int. Cl.
*A61B 5/16* (2006.01)
*A61B 5/00* (2006.01)
*G06K 9/00* (2006.01)

(52) U.S. Cl.
CPC ............ *A61B 5/165* (2013.01); *A61B 5/0022* (2013.01); *A61B 5/167* (2013.01); *G06K 9/00288* (2013.01)

(58) Field of Classification Search
CPC ....... A61B 5/165; A61B 5/0022; A61B 5/167; A61B 5/0077; A61B 5/6898;
(Continued)

(56) References Cited

U.S. PATENT DOCUMENTS

2006/0093189 A1* 5/2006 Kato .................. G06K 9/00335
382/107
2012/0083671 A1* 4/2012 Kato ...................... A61B 5/744
600/301

(Continued)

FOREIGN PATENT DOCUMENTS

JP       2007249953 A   *  9/2007
JP       2009-208727         9/2009
(Continued)

*Primary Examiner* — Nizar N Sivji

(74) *Attorney, Agent, or Firm* — Greenblum & Bernstein, P.L.C.

(57) ABSTRACT

An information processing method includes, by a computer: acquiring biological information on a first person; acquiring an image obtained by imaging the first person in synchronization with acquisition timing of the biological information; identifying person identification information for identifying the first person based on the image; storing, in a storage unit, the identified person identification information, the acquired biological information, and the acquired image in association with one another; acquiring the person identification information on the first person selected by a second person different from the first person, and state information indicating a state of the first person selected by the second person; and extracting, from the storage unit, the image associated with the acquired person identification information and the biological information corresponding to the acquired state information.

13 Claims, 18 Drawing Sheets

(58) Field of Classification Search
CPC ... A61B 2503/06; A61B 5/1176; A61B 5/026; A61B 5/0205; A61B 5/0476; A61B 5/01; G06K 9/00288; G06K 9/00335; H04L 67/06; H04L 67/025; H04L 67/12

See application file for complete search history.

(56) References Cited

U.S. PATENT DOCUMENTS

| | | | |
|---|---|---|---|
| 2015/0061825 A1* | 3/2015 | Suzuki | H04W 4/21 340/5.52 |
| 2015/0127265 A1* | 5/2015 | Iizuka | A61B 5/1118 702/19 |
| 2018/0184959 A1* | 7/2018 | Takahashi | A61B 5/0022 |
| 2018/0285544 A1* | 10/2018 | Chang | G06K 9/00892 |
| 2019/0150858 A1* | 5/2019 | Ishikawa | A61B 5/024 |

FOREIGN PATENT DOCUMENTS

| | | | | |
|---|---|---|---|---|
| JP | 2010282148 A | * | 12/2010 | |
| JP | 2015-046065 | | 3/2015 | |
| JP | 2015-122005 | | 7/2015 | |
| WO | WO-2016051790 A1 | * | 4/2016 | G06F 21/32 |
| WO | 2016/170810 | | 10/2016 | |

\* cited by examiner

FIG.6

| CHILD ID-1 | | |
|---|---|---|
| TIME | CAPTURED IMAGE | BIOLOGICAL INFORMATION |
| t1 | FILE 1 | NUMERICAL VALUE |
| t2 | FILE 2 | NUMERICAL VALUE |
| t3 | FILE 3 | NUMERICAL VALUE |
| ... | ... | ... |

FIG.16

| CHILD ID-1 | | | |
|---|---|---|---|
| TIME | CAPTURED IMAGE | BIOLOGICAL INFORMATION | PLAYING TOOL IDENTIFICATION INFORMATION |
| t1 | FILE 1 | NUMERICAL VALUE | BUILDING BLOCKS |
| t2 | FILE 2 | NUMERICAL VALUE | PICTURE BOOK |
| t3 | FILE 3 | NUMERICAL VALUE | SWING |
| ... | ... | ... | ... |

INFORMATION PROCESSING METHOD, INFORMATION PROCESSING DEVICE, AND INFORMATION PROCESSING SYSTEM

FIELD OF THE INVENTION

The present disclosure relates to an information processing method, an information processing device, and an information processing system that extract predetermined images.

BACKGROUND ART

Conventionally, a nursery-school teacher who takes care of a child in an establishment such as a kindergarten and a nursery school records daily behavior of the child and checks a change in an interest of the child and a change in how the child plays to use the record for supporting parents raising the child.

For example, a play behavior recognition system disclosed in Japanese Patent Application Laid-Open No. 2015-122005 includes: a playing tool that is freely movable in a space and outputs acceleration; a distance image sensor that acquires a position and a posture of a child who moves freely in a space; and a central control device that recognizes a first play behavior classified according to a social behavioral pattern of the child and a second play behavior classified according to mental functions by using the position and the posture of the child and acceleration of the playing tool.

In Japanese Patent Application Laid-Open No. 2015-122005, a nursery-school teacher can appropriately grasp what kind of play behavior the child performs by checking two types of recognized play behavior.

However, although the conventional technique can grasp what kind of play behavior the child performs, it is difficult to identify play behavior that attracts interest of the child or to provide an image indicating a state of the child when the child is performing the play behavior that attracts interest, and further improvement is needed.

SUMMARY OF THE INVENTION

The present disclosure has been made in order to solve the above-described problem, and an object of the present disclosure is to provide an information processing method, an information processing device, and an information processing system that can identify behavior that attracts interest of a first person and provide an image indicating a state of the first person when the first person is performing the behavior that attracts interest.

An information processing method according to one aspect of the present disclosure includes, by a computer: acquiring biological information on a first person; acquiring an image obtained by imaging the first person in synchronization with acquisition timing of the biological information; identifying person identification information for identifying the first person based on the image; storing, in a storage unit, the identified person identification information, the acquired biological information, and the acquired image in association with one another, acquiring the person identification information on the first person selected by a second person different from the first person, and state information indicating a state of the first person selected by the second person; and extracting, from the storage unit, the image associated with the acquired person identification information and the biological information corresponding to the acquired state information.

BRIEF DESCRIPTION OF THE DRAWINGS

FIG. 6 is a diagram showing one example of data structure of an image DB in the first embodiment of the present disclosure;

FIG. 16 is a diagram showing one example of data structure of an image DB in the third embodiment of the present disclosure;

DESCRIPTION OF EMBODIMENTS

Figure 1:
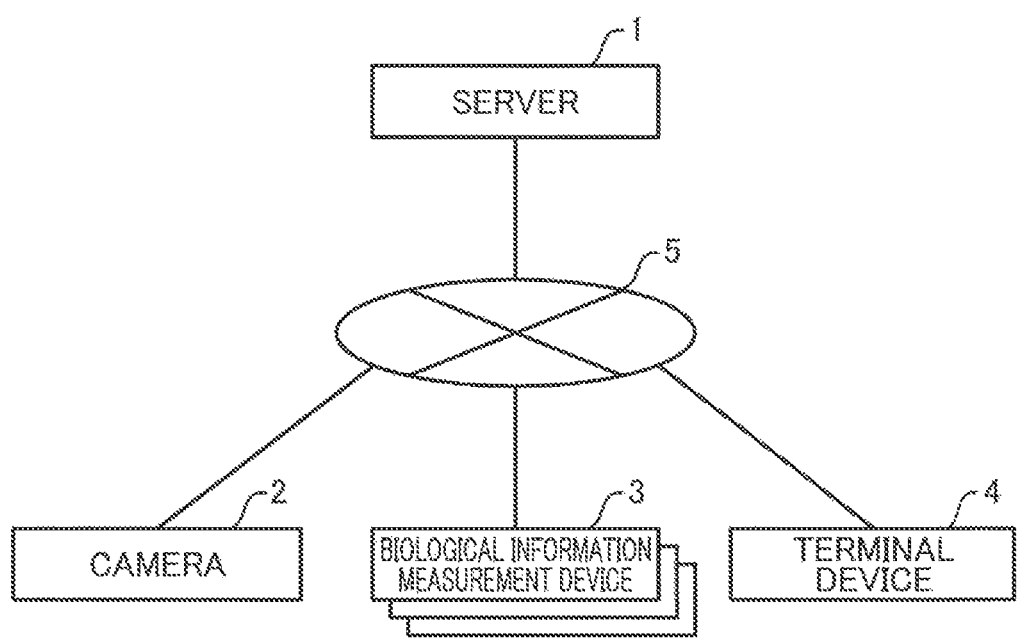
FIG. 1 is a diagram showing one example of a configuration of an information processing system according to a first embodiment of the present disclosure.

Underlying Knowledge Forming Basis of the Present Disclosure

As described above, a nursery-school teacher who takes care of a child in an establishment such as a kindergarten and a nursery school creates a daily childcare record that records daily behavior of the child and checks a change in an interest of the child and a change in how the child plays. At this time, the nursery-school teacher needs to create daily childcare records for children, and needs a lot of time for creating the daily childcare records.

Although the conventional technique can grasp what kind of play behavior the child performs, it is difficult to identify play behavior that attracts interest of the child or to provide an image indicating a state of the child when the child is performing the play behavior that attracts interest.

To solve the above-described problem, an information processing method according to one aspect of the present disclosure includes, by a computer: acquiring biological information on a first person; acquiring an image obtained by imaging the first person in synchronization with acquisition timing of the biological information; identifying person identification information for identifying the first person based on the image; storing, in a storage unit, the identified person identification information, the acquired biological information, and the acquired image in association with one another; acquiring the person identification information on the first person selected by a second person different from the first person, and state information indicating a state of the first person selected by the second person; and extracting, from the storage unit, the image associated with the acquired person identification information and the biological information corresponding to the acquired state information.

With this configuration, the biological information on the first person is acquired. The image obtained by imaging the first person is acquired in synchronization with the acquisition timing of the biological information. The person identification information for identifying the first person is identified based on the image. The identified person identification information, the acquired biological information, and the acquired image are stored in the storage unit in association with one another. The person identification information on the first person selected by the second person different from the first person, and the state information indicating the state of the first person selected by the second person are acquired. The image associated with the acquired person identification information and the biological information corresponding to the acquired state information are extracted from the storage unit.

Therefore, the image associated with the person identification information on the first person selected by the second person, and the biological information corresponding to the state information indicating the state of the first person selected by the second person are extracted from the storage unit. Therefore, it is possible to identify behavior that attracts interest of the first person and to provide the image indicating the state of the first person when the first person is performing the behavior that attracts interest.

In the information processing method, the state information may include psychological state information indicating a psychological state of the first person.

With this configuration, the image associated with the person identification information on the first person and the biological information corresponding to the psychological state information indicating the psychological state of the first person is extracted from the storage unit. Therefore, the image according to the psychological state of first person can be extracted.

In the information processing method, furthermore, the extracted image may be transmitted to a terminal device the second person uses.

With this configuration, since the extracted image is transmitted to the terminal device the second person uses, the second person can check the image according to the state of the first person selected by the second person by using the terminal device.

In the information processing method, furthermore, the extracted image, a date when the image is acquired, and the acquired person identification information may be stored in the storage unit in association with one another, and furthermore, the past image associated with the acquired person identification information may be extracted from the storage unit as a history image.

With this configuration, the extracted image, the date when the image is acquired, and the acquired person identification information are stored in association with one another in the storage unit. Then, the past image associated with the acquired person identification information is extracted from the storage unit as the history image.

Therefore, the image associated with the person identification information on the first person selected by the second person, and the biological information corresponding to the state information indicating the state of the first person selected by the second person is extracted from the storage unit, and the past image associated with the person identification information is extracted from the storage unit as the history image. Therefore, it is possible to provide the image indicating the state of the first person when the first person is performing behavior that attracts interest, and to provide the history image indicating the past state of the first person.

In the information processing method, furthermore, the extracted history image together with the extracted image may be transmitted to a terminal device the second person uses.

With this configuration, since the extracted history image together with the extracted image is transmitted to the terminal device the second person uses, the second person can check the image according to the state of the first person selected by the second person, and the history image indicating the past state of the first person by using the terminal device. Also, the second person can compare the image provided this time with the history image.

In the information processing method, a code having the person identification information may be attached to a surface of the first person, and identifying the person identification information may include identifying the person identification information by reading the code within the image.

With this configuration, the code having the person identification information is attached to the surface of the first person. In the identification of the person identification information, the person identification information is identified by reading the code within the image.

Therefore, the person identification information on the first person who exists within the image can be easily identified by reading the code attached to the surface of the first person within the image.

In the information processing method, identifying the person identification information may include identifying the person identification information by authenticating a face of the first person within the image.

With this configuration, in the identification of the person identification information, the person identification information is identified by authenticating the face of the first person within the image.

Therefore, the person identification information on the first person who exists within the image can be easily identified by authenticating the face of the first person within the image.

In the information processing method, furthermore, playing tool identification information for identifying a playing tool may be identified based on the image, the storing may include storing, in the storage unit, the person identification information, the biological information, the image, and the playing tool identification information in association with one another, and the extracting may include extracting, from the storage unit, the image and the playing tool identification information associated with the acquired person identification information and the biological information corresponding to the acquired state information.

With this configuration, the playing tool identification information for identifying the playing tool is identified based on the image. In the storage, the person identification information, the biological information, the image, and the playing tool identification information are stored in association with one another in the storage unit. In the extraction, the image and the playing tool identification information associated with the acquired person identification information and the biological information corresponding to the acquired state information are extracted from the storage unit.

Therefore, the image and the playing tool identification information associated with the person identification information on the first person selected by the second person and the biological information corresponding to the state information indicating the state of the first person selected by the second person are extracted from the storage unit. Therefore, it is possible to identify the behavior and the playing tool that attract interest of the first person, and to provide the image indicating the state of the first person when the first person is performing the behavior that attracts interest and the playing tool identification information that identifies the playing tool that attracts interest of the first person.

In the information processing method, a code having the playing tool identification information may be attached to a surface of the playing tool, and identifying the playing tool identification information may include identifying the playing tool identification information by reading the code within the image.

With this configuration, the code having the playing tool identification information is attached to the surface of the playing tool. In the identification of the playing tool identification information, the playing tool identification information is identified by reading the code within the image.

Therefore, the playing tool identification information on the playing tool that exists within the image can be easily identified by reading the code attached to the surface of the playing tool within the image.

In the information processing method, identifying the person identification information may include further identifying a position of the first person within the image, identifying the playing tool identification information may include further identifying a position of the playing tool within the image, and further identifying a position of the playing tool within a past image acquired before the acquired image in terms of time, and the storing may include storing, in the storage unit, the playing tool identification information on the playing tool with a distance between the position of the first person and the position of the playing tool within the image shorter than a predetermined threshold and the position moving, the person identification information, the biological information, and the image in association with one another.

With this configuration, in the identification of the person identification information, the position of the first person within the image is further identified. In the identification of the playing tool identification information, the position of the playing tool within the image is further identified, and the position of the playing tool within the past image acquired before the acquired image in terms of time is further identified. In the storage, the playing tool identification information on the playing tool with a distance between the position of the first person and the position of the playing tool within the image shorter than a predetermined threshold and the position moving, the person identification information, the biological information, and the image are stored in association with one another in the storage unit.

Therefore, since it is possible to estimate that the playing tool near the first person and having the moving position is the playing tool the first person uses, the playing tool the first person uses can be identified more securely.

In the information processing method, identifying the person identification information may include further identifying a position of the first person within the image, identifying the playing tool identification information may include further identifying a position of the playing tool within the image, and the storing may include storing, in the storage unit, the playing tool identification information on the playing tool with a distance between the position of the first person and the position of the playing tool shorter than a predetermined threshold, the person identification information, the biological information, and the image in association with one another.

With this configuration, in the identification of the person identification information, the position of the first person within the image is further identified. In the identification of the playing tool identification information, the position of the playing tool within the image is further identified. In the storage, the playing tool identification information on the playing tool with a distance between the position of the first person and the position of the playing tool shorter than a predetermined threshold, the person identification information, the biological information, and the image are stored in association with one another in the storage unit.

Therefore, since it is possible to estimate that the playing tool near the first person is the playing tool the first person uses, the playing tool the first person uses can be identified easily.

An information processing device according to another aspect of the present disclosure includes: a communication unit; a processor; and a memory, wherein the communication unit acquires biological information on a first person, the communication unit acquires an image obtained by imaging the first person in synchronization with acquisition timing of the biological information, the processor identifies person identification information for identifying the first person based on the image, the processor stores, in the memory, the identified person identification information, the acquired biological information, and the acquired image in association with one another, the communication unit acquires the person identification information on the first person selected by a second person different from the first person, and state information indicating a state of the first person selected by the second person, and the processor extracts, from the memory, the image associated with the acquired person identification information and the biological information corresponding to the acquired state information.

With this configuration, the communication unit acquires biological information on a first person. The communication unit acquires an image obtained by imaging the first person in synchronization with acquisition timing of the biological information. The processor identifies person identification information for identifying the first person based on the image. The processor stores, in the memory, the identified person identification information, the acquired biological information, and the acquired image in association with one another. The communication unit acquires the person identification information on the first person selected by a second person different from the first person, and state information indicating a state of the first person selected by the second person. The processor extracts, from the memory, the image associated with the acquired person identification information and the biological information corresponding to the acquired state information.

Therefore, the image associated with the person identification information on the first person selected by the second person, and the biological information corresponding to the state information indicating the state of the first person selected by the second person are extracted from the storage unit. Therefore, it is possible to identify behavior that attracts interest of the first person and to provide the image indicating the state of the first person when the first person is performing the behavior that attracts interest.

An information processing system according to another aspect of the present disclosure includes: a camera; a biological information measurement device; an information processing device; and a terminal device, wherein the camera includes: an image capturing unit that images a first person; and a transmitter that transmits an image captured by the image capturing unit to the information processing device, the biological information measurement device includes: a measurement unit that measures biological information on the first person; and a transmitter that transmits the biological information measured by the measurement unit to the information processing device, the information processing device includes: a storage unit; a first acquisition unit that acquires the biological information transmitted by the biological information measurement device; a second acquisition unit that acquires the image transmitted by the camera in synchronization with acquisition timing of the biological information; an identification unit that identifies person identification information for identifying the first person based on the image; a storage execution unit that stores, in the storage unit, the identified person identification information, the acquired biological information, and the acquired image in association with one another; a third acquisition unit that acquires, from the terminal device, the person identification information on the first person selected by a second person different from the first person, and state information indicating a state of the first person selected by the second person; an extraction unit that extracts, from the storage unit, the image associated with the acquired person identification information and the biological information corresponding to the acquired state information; and a transmitter that transmits the extracted image to the terminal device, the terminal device includes: an input reception unit that receives input, made by the second person, of the person identification information on the first person, and the state information indicating the state of the first person; a transmitter that transmits the input person identification information and the state information to the information processing device; a reception unit that receives the image transmitted by the information processing device; and a display unit that displays the image received by the reception unit.

With this configuration, the image capturing unit of the camera images the first person. The transmitter of the camera transmits the image captured by the image capturing unit to the information processing device. The measurement unit of the biological information measurement device measures the biological information on the first person. The transmitter of the biological information measurement device transmits the biological information measured by the measurement unit to the information processing device. The first acquisition unit of the information processing device acquires the biological information transmitted by the biological information measurement device. The second acquisition unit of the information processing device acquires the image transmitted by the camera in synchronization with acquisition timing of the biological information. The identification unit of the information processing device identifies the person identification information for identifying the first person based on the image. The storage execution unit of the information processing device stores, in the storage unit, the identified person identification information, the acquired biological information, and the acquired image in association with one another. The third acquisition unit of the information processing device acquires, from the terminal device, the person identification information on the first person selected by the second person different from the first person, and the state information indicating the state of the first person selected by the second person. The extraction unit of the information processing device extracts, from the storage unit, the image associated with the acquired person identification information and the biological information corresponding to the acquired state information. The transmitter of the information processing device transmits the extracted image to the terminal device. The input reception unit of the terminal device receives input, made by the second person, of the person identification information on the first person, and the state information indicating the state of the first person. The transmitter of the terminal device transmits the input person identification information and the state information to the information processing device. The reception unit of the terminal device receives the image transmitted by the information processing device. The display unit of the terminal device displays the image received by the reception unit.

Therefore, the image associated with the person identification information on the first person selected by the second person, and the biological information corresponding to the state information indicating the state of the first person selected by the second person are extracted from the storage unit. Therefore, it is possible to identify behavior that attracts interest of the first person and to provide the image indicating the state of the first person when the first person is performing the behavior that attracts interest.

Embodiments of the present disclosure will be described below with reference to the accompanying drawings. Note that the following embodiments are one example embodying the present disclosure, and do not limit the technical scope of the present disclosure.

First Embodiment

FIG. 1 is a diagram showing one example of a configuration of an information processing system according to a first embodiment of the present disclosure. The information processing system shown in FIG. 1 includes a server 1, a camera 2, a plurality of biological information measurement devices 3, and a terminal device 4.

Note that the present first embodiment describes an example in which a nursery-school teacher takes care of a child and creates a daily childcare record for the child in a kindergarten or a nursery school.

The server 1 is communicatively connected to each of the camera 2, the plurality of biological information measurement devices 3, and the terminal device 4 via a network 5. The network 5 is, for example, the Internet.

The camera 2 is installed indoors or outdoors, and captures children to be taken care of. Note that the information processing system in the present first embodiment may include a plurality of cameras 2 instead of including one camera 2.

The plurality of biological information measurement devices 3 is, for example, smart watches, and is worn on the children. Each of the plurality of biological information measurement devices 3 measures biological information on the child.

Note that in the present first embodiment, although the information processing system includes the plurality of biological information measurement devices 3, if one biological information measurement device 3 can measure biological information on children, the information processing system may include one biological information measurement device 3.

The terminal device 4 is, for example, a smart phone, a tablet computer, or a personal computer, receives various information items from the server 1, and transmits various information items to the server 1. The nursery-school teacher (second person) uses the terminal device 4.

Figure 2:
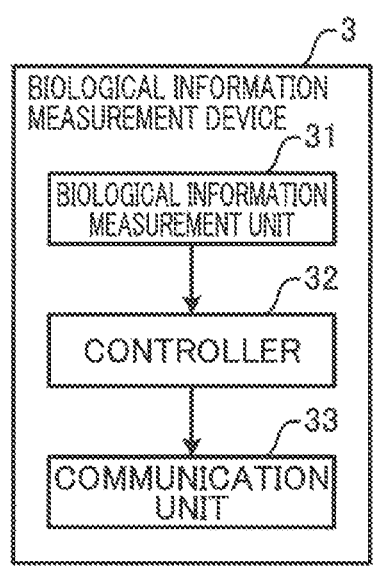
FIG. 2 is a diagram showing a configuration of a biological information measurement device in the first embodiment of the present disclosure.

FIG. 2 is a diagram showing a configuration of the biological information measurement device in the first embodiment of the present disclosure. The biological information measurement device 3 shown in FIG. 2 includes a biological information measurement unit 31, a controller 32, and a communication unit 33.

The biological information measurement unit 31 is, for example, various types of sensor, and measures biological information on a child (first person). The biological information measurement unit 31 measures the biological information on the child at predetermined time intervals. The biological information is, for example, at least one of a child's blood flow, heart rate, pulse rate, brain waves, blood pressure, pulse wave, living body gas, breathing, and body temperature.

The controller 32 is, for example, a central processing unit (CPU), and controls the overall biological information measurement device 3.

The communication unit 33 transmits the biological information measured by the biological information measurement unit 31 to the server 1. The communication unit 33 regularly transmits the biological information to the server 1 at predetermined time intervals (for example, at one-second intervals). At this time, the communication unit 33 transmits person identification information for identifying the child to measure, together with the biological information.

Note that although the information processing system in the present first embodiment includes the contact biological information measurement device 3, the information processing system may include the contactless biological information measurement device 3. The contactless biological information measurement device 3 measures a pulse wave of a child in a contactless manner by using, for example, a highly sensitive spread-spectrum millimeter-wave radar, and detects a heart rate and heart rate variability of the child.

Figure 3:
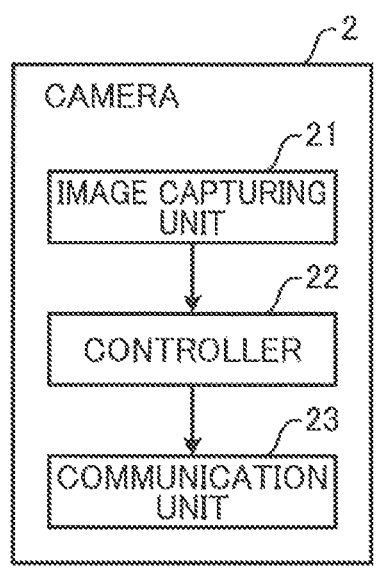
FIG. 3 is a diagram showing a configuration of a camera in the first embodiment of the present disclosure.

FIG. 3 is a diagram showing a configuration of the camera in the first embodiment of the present disclosure. The camera 2 shown in FIG. 3 includes an image capturing unit 21, a controller 22, and a communication unit 23.

The image capturing unit 21 images a child. The image capturing unit 21 images a child at predetermined time intervals (for example, at one-second intervals). When the camera 2 is installed indoors, the camera 2 is installed on a ceiling of a room in which the child is present, and when the camera 2 is installed outdoors, the camera 2 is installed at a position where the camera 2 can image a place where a child is present from a high place.

The controller 22 is, for example, a CPU, and controls the overall camera 2.

The communication unit 23 transmits an image captured by the image capturing unit 21 to the server 1. Note that in the present first embodiment, the communication unit 23 transmits a still image captured at predetermined time intervals to the server 1 at predetermined time intervals (for example, at one-second intervals). However, the present disclosure is not particularly limited to this example, and the communication unit 23 may transmit a moving image to the server 1.

Figure 4:
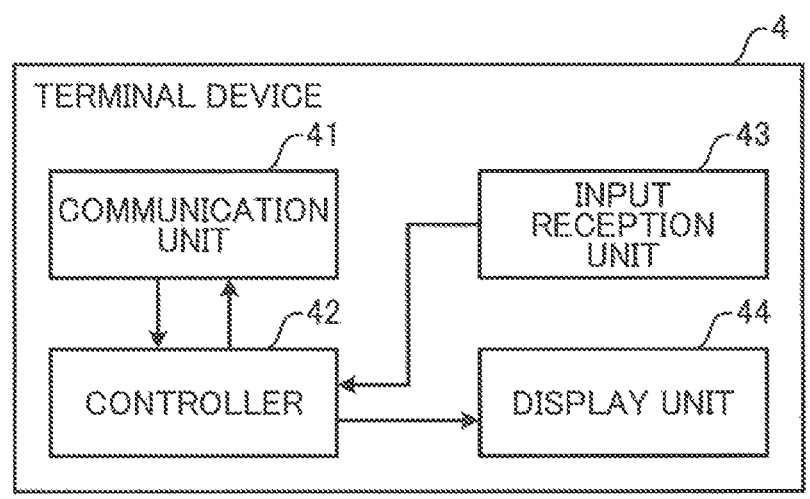
FIG. 4 is a diagram showing a configuration of a terminal device in the first embodiment of the present disclosure.

FIG. 4 is a diagram showing a configuration of the terminal device in the first embodiment of the present disclosure. The terminal device 4 shown in FIG. 4 includes a communication unit 41, a controller 42, an input reception unit 43, and a display unit 44.

The input reception unit 43 is, for example, a touch panel, a keyboard, or a mouse, and receives information input made by the nursery-school teacher (second person) different from the child (first person). The input reception unit 43 receives input made by the nursery-school teacher about the person identification information for identifying the child and state information indicating a state of the child. When creating the daily childcare record for the child, the nursery-school teacher designates the child for whom to create the daily childcare record, and designates the state of the child necessary for extracting an image to attach to the daily childcare record.

The communication unit 41 transmits, to the server 1, a daily childcare record creation instruction for creating the daily childcare record. The daily childcare record creation instruction includes the person identification information and the state information which are input by the input reception unit 43. By transmitting the daily childcare record creation instruction to the server 1, the communication unit 41 transmits, to the server 1, the person identification information and the state information which are input by the input reception unit 43. Also, the communication unit 41 receives a candidate image transmitted by the server 1.

The controller 42 is, for example, a CPU, and controls the overall terminal device 4.

The display unit 44 is, for example, a liquid crystal display device, and displays the image received by the communication unit 41. Note that when the communication unit 41 receives a plurality of candidate images, the display unit 44 may display the plurality of received candidate images, and the input reception unit 43 may receive selection made by the nursery-school teacher about the desired candidate image from among the plurality of candidate images. At this time, the nursery-school teacher may select one candidate image to attach to the daily childcare record from among the plurality of candidate images, and may select two or more candidate images to attach to the daily childcare record. Also, when the communication unit 41 receives one candidate image, the display unit 44 may display the received one candidate image, and the input reception unit 43 may receive determination made by the nursery-school teacher about whether to attach the one candidate image to the daily childcare record.

The communication unit 41 transmits image selection information for identifying the candidate image selected by the input reception unit 43 to the server 1. Also, the communication unit 41 receives a daily record image transmitted by the server 1.

Figure 5:
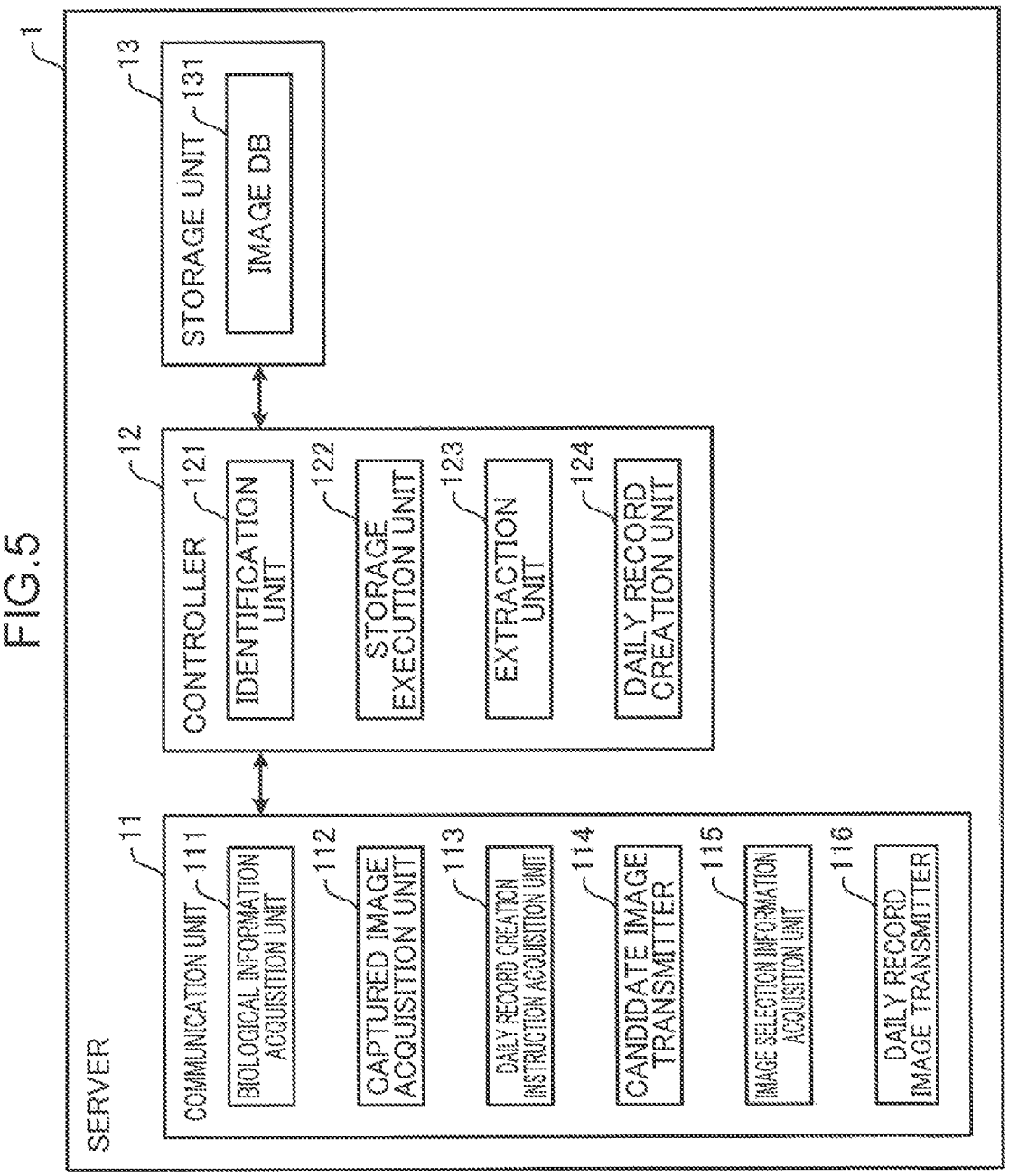
FIG. 5 is a diagram showing a configuration of a server in the first embodiment of the present disclosure.

FIG. 5 is a diagram showing a configuration of the server in the first embodiment of the present disclosure. The server 1 shown in FIG. 5 includes a communication unit 11, a controller 12, and a storage unit 13.

The communication unit 11 includes a biological information acquisition unit 111, a captured image acquisition unit 112, a daily record creation instruction acquisition unit 113, a candidate image transmitter 114, an image selection information acquisition unit 115, and a daily record image transmitter 116. The controller 12 is, for example, a CPU, and includes an identification unit 121, a storage execution unit 122, an extraction unit 123, and a daily record creation unit 124. The storage unit 13 is, for example, a semiconductor memory, and includes an image database (DB) 131.

The biological information acquisition unit 111 acquires the biological information on the child (first person). The biological information acquisition unit 111 regularly receives the biological information transmitted by the biological information measurement devices 3 at predetermined time intervals (for example, at one-second intervals). The biological information acquisition unit 111 outputs, to the storage execution unit 122, the received biological information together with a time stamp indicating time when the biological information is received.

The captured image acquisition unit 112 acquires the image of the child (first person) imaged in synchronization with acquisition timing of the biological information. The captured image acquisition unit 112 regularly receives the captured image transmitted by the camera 2 at predetermined time intervals (for example, at one-second intervals). Note that when the captured image is a still image, the captured image acquisition unit 112 receives the still image in synchronization with acquisition timing of the biological information. Alternatively, when the captured image is a moving image, the captured image acquisition unit 112 extracts the still image from the received moving image in synchronization with acquisition timing of the biological information. The captured image acquisition unit 112 outputs, to the identification unit 121, the received captured image together with a time stamp indicating time when the captured image is received.

Based on the captured image acquired by the captured image acquisition unit 112, the identification unit 121 identifies the person identification information for identifying the child (first person). A code having the person identification information is attached to a surface of the child (first person). By reading the code in the captured image, the identification unit 121 identifies the person identification information included in the captured image.

Note that as the code, for example, Colorbit (registered trademark) is used. Colorbit is consecutive arrangement of cells of a plurality of colors, and is generated by converting the person identification information based on a predetermined standard. By decoding Colorbit within the captured image, the identification unit 121 obtains the person identification information. Colorbit has characteristics of being able to identify positions of Colorbit codes within the captured image, and to read a plurality of Colorbit codes within the captured image collectively. Therefore, by reading the plurality of Colorbit codes within the captured image at the same time, the identification unit 121 can identify the person identification information and the positional information on children at the same time.

The storage execution unit 122 stores, in an image DB 131 of the storage unit 13, the person identification information identified by the identification unit 121, the biological information acquired by the biological information acquisition unit 111, and the captured image acquired by the captured image acquisition unit 112 in association with one another.

FIG. 6 is a diagram showing one example of data structure of the image DB in the first embodiment of the present disclosure. "Child ID-1" of FIG. 6 shows the person identification information on a specified child.

The image DB 131 stores the captured image, the biological information, and time for each piece of person identification information in association with one another. The captured image represents a file name in which the captured image is stored, and the time represents time when the captured image and the biological information are acquired in the server 1. Note that the time may be time when the camera 2 and the biological information measurement devices 3 transmit the captured image and the biological information to the server 1. The biological information is, for example, numerical values such as a heart rate.

The storage execution unit 122 stores the biological information and the captured image acquired at identical time in association with each other in the image DB 131.

The daily record creation instruction acquisition unit 113 acquires the daily record creation instruction including the person identification information on the child (first person) selected by the nursery-school teacher (second person) different from the child (first person), and the state information indicating the state of the child selected by the nursery-school teacher. The daily record creation instruction acquisition unit 113 receives the daily record creation instruction transmitted from the terminal device 4.

The extraction unit 123 extracts, from the image DB 131 of the storage unit 13, the captured image associated with the person identification information acquired by the daily record creation instruction acquisition unit 113 and the biological information corresponding to the state information acquired by the daily record creation instruction acquisition unit 113. For example, the state information includes psychological state information indicating a psychological state of the child (first person). The psychological state is, for example, a state where the degree of excitement is high, or a state where the degree of excitement is low. The state where the degree of excitement is high represents, for example, the state where the heart rate, which is biological information, is equal to or greater than a first threshold, whereas the state where the degree of excitement is low represents, for example, the state where the heart rate, which is biological information, is equal to or less than a second threshold that is lower than the first threshold.

Therefore, when the state information is a state where the degree of excitement of the child is high, the extraction unit 123 extracts at least one captured image associated with the heart rate that is equal to or greater than the first threshold from among a plurality of captured images associated with the acquired person identification information. When the state information is a state where the degree of excitement of the child is low, the extraction unit 123 extracts at least one captured image associated with the heart rate that is equal to or less than the second threshold from among the plurality of captured images associated with the acquired person identification information.

For example, when the state information is a state where the degree of excitement of the child is high, the extraction unit 123 may extract captured images associated with a predetermined number of heart rates in order from the highest value, from among the plurality of captured images associated with the acquired person identification information. For example, when the state information is a state where the degree of excitement of the child is low, the extraction unit 123 may extract captured images associated with the predetermined number of heart rates in order from the lowest value, from among the plurality of captured images associated with the acquired person identification information. The predetermined number is three, for example.

Note that when a plurality of captured images is extracted at short time intervals, it is estimated that the plurality of captured images is images captured when the child is performing the same play and is excited. Therefore, when the plurality of captured images is extracted at predetermined time intervals, the extraction unit 123 may select only one captured image from among the plurality of captured images. Then, the extraction unit 123 may extract remaining captured images at time intervals other than the predetermined time intervals including the time associated with the selected one captured image.

The state where the degree of excitement is high may represent, for example, a state where the heart rate, which is biological information, is highest, whereas the state where the degree of excitement is low may represent, for example, a state where the heart rate, which is biological information, is lowest. When the state information is a state where the degree of excitement of the child is high, the extraction unit 123 may extract the captured image associated with the highest heart rate from among the plurality of captured images associated with the acquired person identification information. When the state information is a state where the degree of excitement of the child is low, the extraction unit 123 may extract the captured image associated with the lowest heart rate from among the plurality of captured images associated with the acquired person identification information.

The state information received from the terminal device 4 may be information indicating feeling of the child, for example, excited state, delighted state, relaxed state, bored state, depressed state, sad state, terrified state, or angered state. In this case, the extraction unit 123 may convert into feeling each of a plurality of pieces of biological information associated with the person identification information in the image DB 131. Then, out of the converted feeling, the extraction unit 123 may extract the captured image associated with the same feeling as feeling indicated by the state information acquired by the daily record creation instruction acquisition unit 113. Note that about a method of converting biological information into feeling, it is possible to use, for example, techniques disclosed in WO 2016/170810, Japanese Patent Application Laid-Open No. 2009-208727, and Japanese Patent Application Laid-Open No. 2015-46065. This makes it possible to extract the captured image captured when feeling of the child is feeling the nursery-school teacher desires, for example, the delighted state.

The candidate image transmitter 114 transmits the captured image extracted by the extraction unit 123 to the terminal device 4 as the candidate image.

The image selection information acquisition unit 115 acquires the image selection information indicating the candidate image selected by the nursery-school teacher. The image selection information acquisition unit 115 receives the image selection information transmitted by the terminal device 4.

The daily record creation unit 124 creates the daily record image in which the candidate image selected by the nursery-school teacher is fitted in a predetermined daily record template based on the image selection information acquired by the image selection information acquisition unit 115. Note that the daily record template is stored in the storage unit 13 in advance.

The daily record image transmitter 116 transmits the daily record image created by the daily record creation unit 124 to the terminal device 4.

Subsequently, an operation of the server 1 in the present first embodiment will be described.

Figure 7:
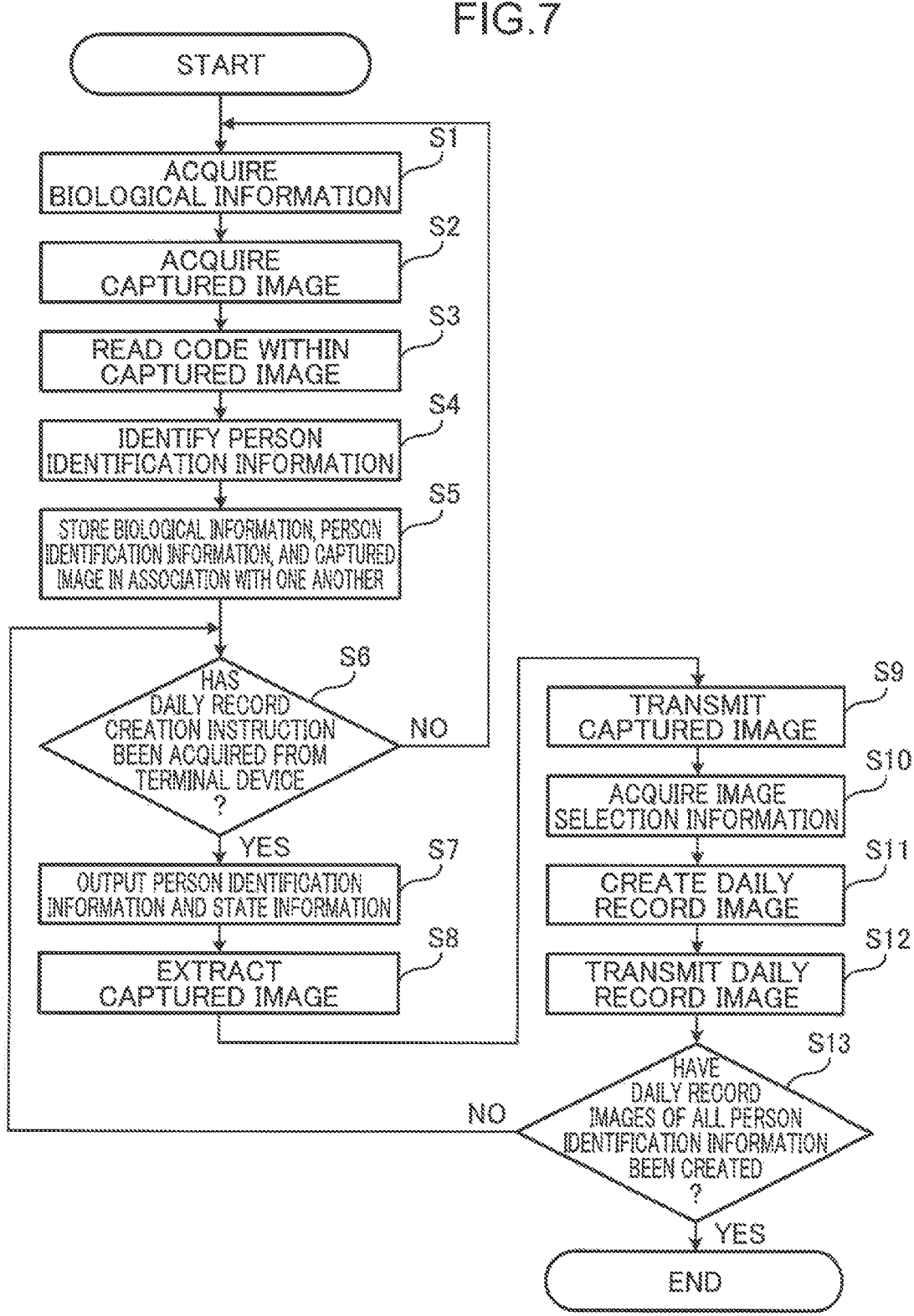
FIG. 7 is a flowchart for describing an operation of the server in the first embodiment of the present disclosure.

FIG. 7 is a flowchart for describing the operation of the server in the first embodiment of the present disclosure.

First, in step S1, the biological information acquisition unit 111 acquires the biological information on the child from the biological information measurement device 3. Note that in the present first embodiment, the biological information is acquired from each of the plurality of biological information measurement devices 3.

Next, in step S2, the captured image acquisition unit 112 acquires, from the camera 2, the captured image obtained by capturing the inside of space in which the child is present. At this time, the captured image acquisition unit 112 acquires the captured image in synchronization with acquisition timing of the biological information. This allows time to acquire the biological information to coincide with time to acquire the captured image.

Next, in step S3, the identification unit 121 reads the code within the captured image acquired by the captured image acquisition unit 112.

Next, in step S4, the identification unit 121 identifies the person identification information included in the captured image.

Next, in step S5, the storage execution unit 122 stores, in the image DB 131 of the storage unit 13, the biological information acquired by the biological information acquisition unit 111, the person identification information identified by the identification unit 121, and the captured image acquired by the captured image acquisition unit 112 in association with one another.

Note that the biological information is acquired but the person identification information included in the captured image is not identified in some cases, because the code attached to the child is in a blind spot of the camera 2. Therefore, the storage execution unit 122 preferably stores, in the image DB 131, the person identification information identified by the identification unit 121, the biological information corresponding to the identified person identification information, the captured image including the identified person identification information, and the time when the captured image and the biological information are acquired, in association with one another.

Next, in step S6, the daily record creation instruction acquisition unit 113 determines whether the daily record creation instruction including the person identification information of the child selected by the nursery-school teacher and the state information indicating the state of the child selected by the nursery-school teacher has been acquired from the terminal device 4. Here, when it is determined that the daily record creation instruction has not been acquired from the terminal device 4 (NO in step S6), the processing returns to step S1.

Figure 8:
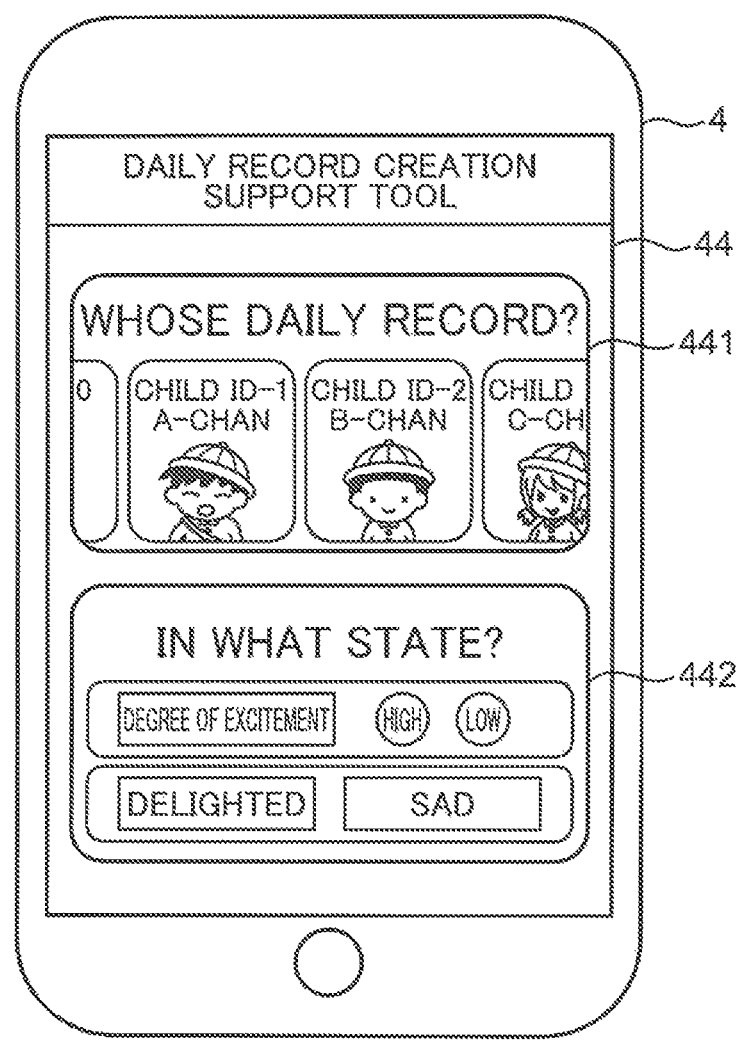
FIG. 8 is a view showing one example of an input screen of a daily record creation instruction in the terminal device in the first embodiment of the present disclosure.

FIG. 8 is a view showing one example of an input screen of the daily record creation instruction in the terminal device in the first embodiment of the present disclosure.

When receiving input of the person identification information on the child and the state information indicating the state of the child from the nursery-school teacher, the display unit 44 of the terminal device 4 displays the input screen shown in FIG. 8. The input screen shown in FIG. 8 includes a first input reception area 441 for receiving the input of the person identification information on the child, and a second input reception area 442 for receiving the input of the state information indicating the state of the child.

The first input reception area 441 selectably displays at least one child image including the person identification information on the child registered in advance, a name of the child, and a face image of the child. The nursery-school teacher selects one child image for creating the daily record from at least one child image displayed on the first input reception area 441. Note that the nursery-school teacher can display the plurality of child images by performing a swipe operation on the first input reception area 441, and select the person identification information on the child for whom to create the daily record by tapping the desired child image. The input reception unit 43 receives an input operation of the nursery-school teacher on the first input reception area 441.

The second input reception area 442 selectably displays at least one piece of state information. For example, in FIG. 8, the nursery-school teacher can select one piece of state information from among the state information indicating the state where the degree of excitement is high, the state information indicating the state where the degree of excitement is low, the state information indicating the delighted state, and the state information indicating the sad state. The nursery-school teacher selects one piece of state information indicating the state of the child necessary for extracting the captured image to put on the daily record from at least one piece of state information displayed on the second input reception area 442. Note that the nursery-school teacher can select the state information on the child by tapping the desired state information. Accordingly, the captured image that agrees with the state of the child designated by the nursery-school teacher is extracted. The input reception unit 43 receives the input operation of the nursery-school teacher on the second input reception area 442.

Figure 9:
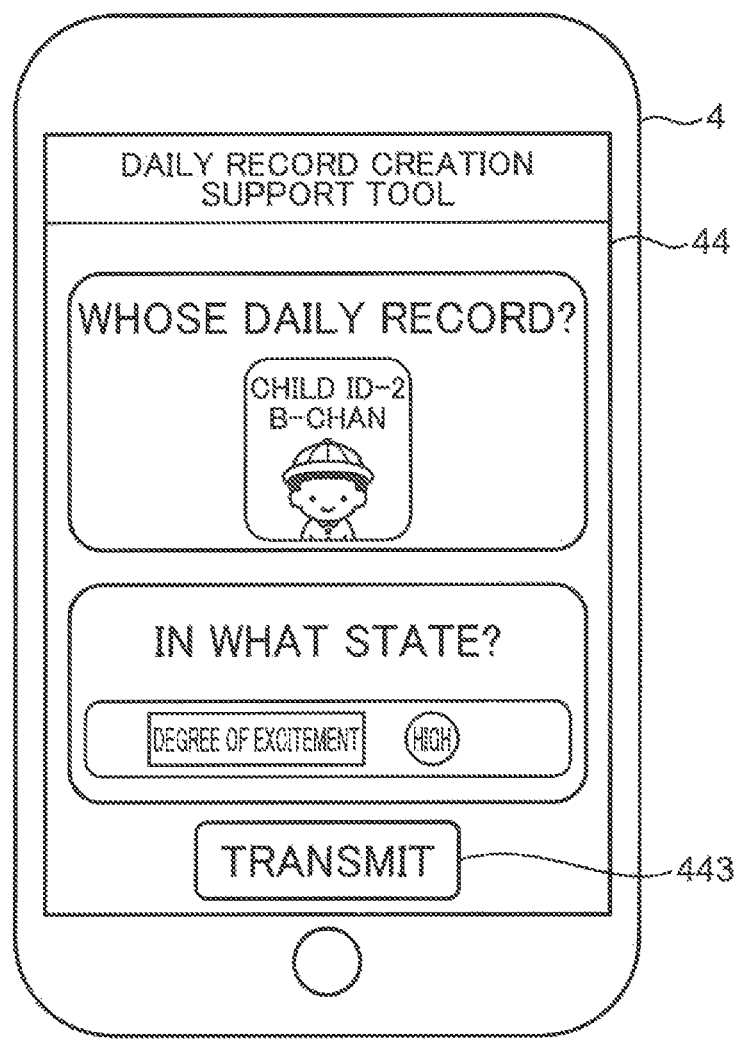
FIG. 9 is a view showing one example of a transmission screen of the daily record creation instruction in the terminal device in the first embodiment of the present disclosure.

FIG. 9 is a view showing one example of a transmission screen of the daily record creation instruction in the terminal device in the first embodiment of the present disclosure.

When transmitting, to the server 1, the daily record creation instruction including the person identification information on the child and the state information indicating the state of the child, the display unit 44 of the terminal device 4 displays the transmission screen shown in FIG. 9. The transmission screen shown in FIG. 9 includes the person identification information selected by the nursery-school teacher, the state information selected by the nursery-school teacher, and a transmission button 443 for receiving input of whether to transmit the daily record creation instruction to the server 1. For example, in FIG. 9, the person identification information corresponding to "Child ID-2" is selected, and the state information indicating the state where the degree of excitement is high is selected. When the displayed person identification information and the state information have no problems, the nursery-school teacher taps the transmission button 443. The input reception unit 43 receives the input operation of the nursery-school teacher on the transmission button 443. When the nursery-school teacher taps the transmission button 443, the communication unit 41 transmits, to the server 1, the daily record creation instruction including the person identification information and the state information that are input by the nursery-school teacher.

Returning to FIG. 7, when it is determined that the daily record creation instruction is acquired from the terminal device 4 (YES in step S6), in step S7, the daily record creation instruction acquisition unit 113 outputs the person identification information and the state information included in the acquired daily record creation instruction to the extraction unit 123.

Next, in step S8, the extraction unit 123 extracts, from the image DB 131 of the storage unit 13, the captured image associated with the person identification information acquired by the daily record creation instruction acquisition unit 113 and the biological information corresponding to the state information acquired by the daily record creation instruction acquisition unit 113. For example, when the acquired state information indicates the state where the degree of excitement is high, the extraction unit 123 extracts the captured image with the heart rate, which is biological information, equal to or greater than a threshold, from among the captured images associated with the acquired person identification information.

Figure 10:
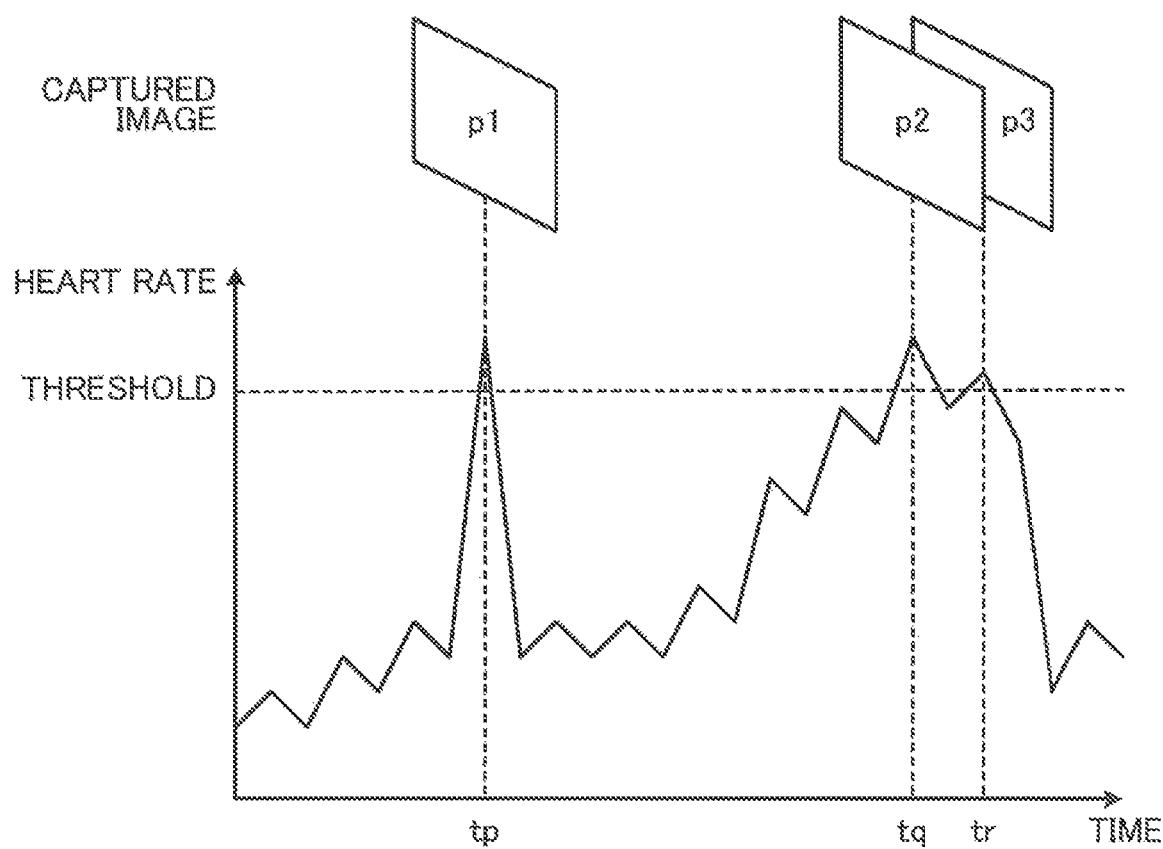
FIG. 10 is a diagram for describing a captured image extracted by an extraction unit in the first embodiment of the present disclosure.

FIG. 10 is a diagram for describing the captured image extracted by the extraction unit in the first embodiment of the present disclosure.

In a graph shown in FIG. 10, a vertical axis represents the heart rate of the child corresponding to the acquired person identification information, whereas a horizontal axis represents time from childcare start time to childcare finish time of the child corresponding to the acquired person identification information. The heart rate is biological information and is acquired at predetermined timing. The captured image is also acquired in synchronization with the timing when the heart rate is acquired. In FIG. 10, the heart rate is equal to or greater than a threshold at time tp, time tq, and time tr. In this case, from among the plurality of captured images associated with the acquired person identification information, the extraction unit 123 extracts the captured images p1, p2, and p3 at time tp, tq, and tr, respectively, at which the heart rate is equal to or greater than the threshold.

Returning to FIG. 7, next, in step S9, the candidate image transmitter 114 transmits the captured image extracted by the extraction unit 123 to the terminal device 4 as the candidate image. The communication unit 41 of the terminal device 4 receives the candidate image transmitted by the server 1. The display unit 44 displays the candidate image received by the communication unit 41.

FIG. 1 is a view showing one example of a selection screen that receives selection of the candidate image in the terminal device in the first embodiment of the present disclosure.

Figure 11:
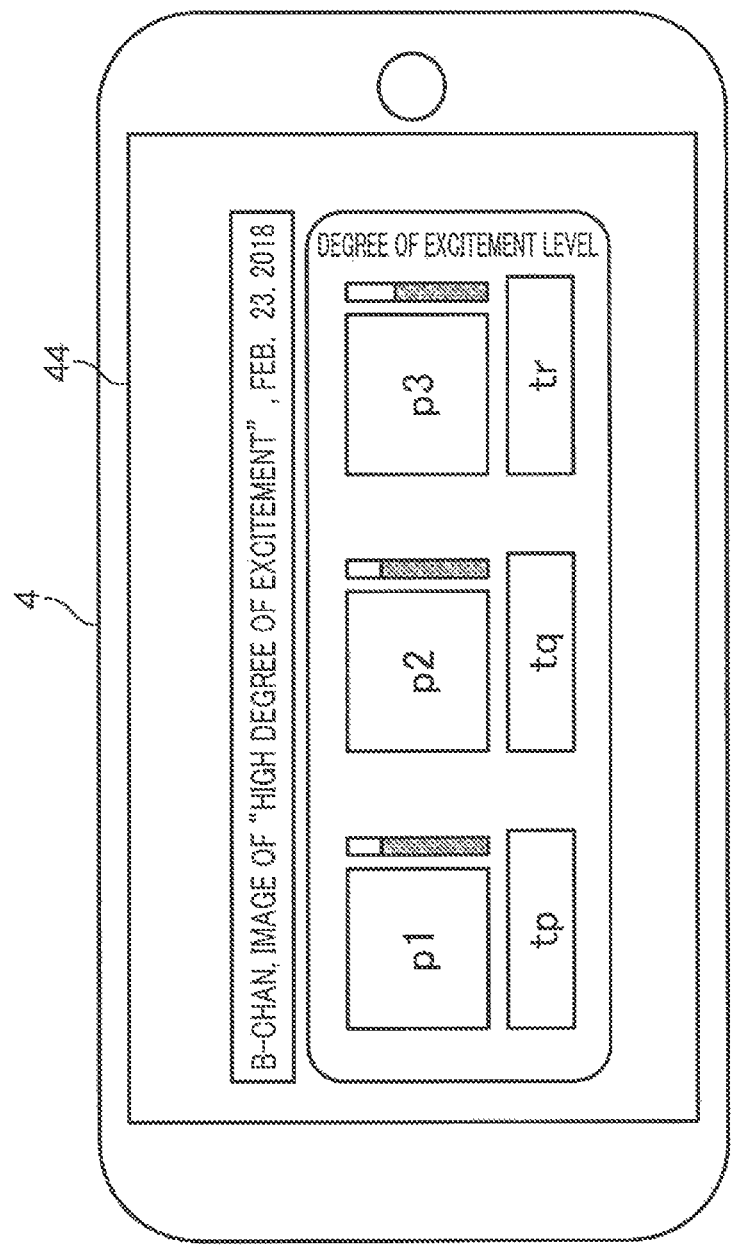
FIG. 11 is a view showing one example of a selection screen that receives selection of a candidate image in the terminal device in the first embodiment of the present disclosure.

When the candidate image transmitted by the server 1 is received, the display unit 44 of the terminal device 4 displays the selection screen shown in FIG. 11. The selection screen shown in FIG. 11 includes the name of the child, the state of the child, today's date, at least one candidate image, time when each candidate image is acquired, and the excitement degree level indicating to what degree the child is excited.

In FIG. 11, the name of the child "B-chan", the state of the child indicating that the degree of excitement is high, the date "Feb. 23, 2018", the candidate images p1, p2, and p3, the time tp, tq, and tr, and the excitement degree level are displayed. The excitement degree level is displayed according to magnitude of the heart rate. These pieces of information are received from the server 1 together with the candidate image. That is, the candidate image transmitter 114 transmits, to the terminal device 4, the name of the child corresponding to the person identification information, the state information, today's date, at least one candidate image, the time associated with each candidate image, and the biological information associated with each candidate image. The communication unit 41 of the terminal device 4 receives these pieces of information transmitted by the server 1.

The nursery-school teacher selects the candidate image to be put on the daily record by tapping the desired candidate image among the plurality of candidate images p1, p2, and p3 displayed on the selection screen. The input reception unit 43 receives a selection operation of the nursery-school teacher on the candidate image. When the candidate image is tapped by the nursery-school teacher, the communication unit 41 transmits the image selection information indicating the selected candidate image to the server 1. Note that the image selection information may be the selected candidate image, or may be information for identifying the selected candidate image.

Returning to FIG. 7, next, in step S10, the image selection information acquisition unit 115 acquires the image selection information transmitted by the terminal device 4.

Next, in step S11, the daily record creation unit 124 creates the daily record image obtained by fitting in the predetermined daily record template the candidate image selected by the nursery-school teacher, the candidate image being indicated by the image selection information acquired by the image selection information acquisition unit 115. The daily record image includes, for example, today's date when the daily record is created, and the candidate image selected by the nursery-school teacher. Note that information to be included in the daily record image is not limited to the above-described information, but the daily record image may also include a character entry field in which the nursery-school teacher can write. Also, the daily record creation unit 124 may store the created daily record image in the storage unit 13.

Next, in step S12, the daily record image transmitter 116 transmits the daily record image created by the daily record creation unit 124 to the terminal device 4. The communication unit 41 of the terminal device 4 receives the daily record image transmitted by the server 1. The display unit 44 displays the daily record image received by the communication unit 41.

When the daily record image transmitted by the server 1 is received, the display unit 44 of the terminal device 4 displays the daily record image. When the daily record image includes the character entry field, the nursery-school teacher inputs characters into the character entry field displayed on the daily record image. The input reception unit 43 receives the input operation of the nursery-school teacher into the character entry field. When the characters are input by the nursery-school teacher, the controller 42 stores, in the storage unit (not shown), the daily record image with the characters input into the character entry field. Note that the communication unit 41 may transmit, to the server 1, the daily record image with the characters input into the character entry field. In this case, the communication unit 11 of the server 1 may receive the daily record image transmitted by the terminal device 4, and store the received daily record image in the storage unit 13.

Note that after the controller 42 stores, in the storage unit, the daily record image with the characters input into the character entry field, the display unit 44 displays the input screen (FIG. 8) for receiving input of the person identification information on another child and the state information indicating the state of another child from the nursery-school teacher. This allows the daily record of another child to be created.

Next, in step S13, the daily record creation unit 124 determines whether the daily record images of all the person identification information have been created. Here, when it is determined that the daily record images of all the person identification information have been created (YES in step S13), the processing ends.

On the other hand, when it is determined that the daily record images of all the person identification information have not been created (NO in step S13), the processing returns to step S6.

In this way, the present first embodiment can identify play behavior that attracts interest of the child, and provide an image indicating the state of the child when the child is performing the play behavior that attracts interest of the child. As a result, the present first embodiment can assist creation of the daily record by the nursery-school teacher, increase efficiency in work to create the daily record, and reduce the work to create the daily record.

Note that in the present first embodiment, the identification unit 121 identifies the person identification information by reading the code within the captured image. However, the present disclosure is not particularly limited to this example, and the identification unit 121 may identify the person identification information by authenticating the face of the child (first person) within the captured image. In this case, the storage unit 13 stores in advance the face image of the child and the person identification information in association with each other.

Second Embodiment

The first embodiment presents the captured images extracted based on the biological information to the terminal device. The second embodiment presents the captured images selected by a nursery-school teacher in the past together with the captured images extracted based on the biological information to the terminal device.

Figure 12:
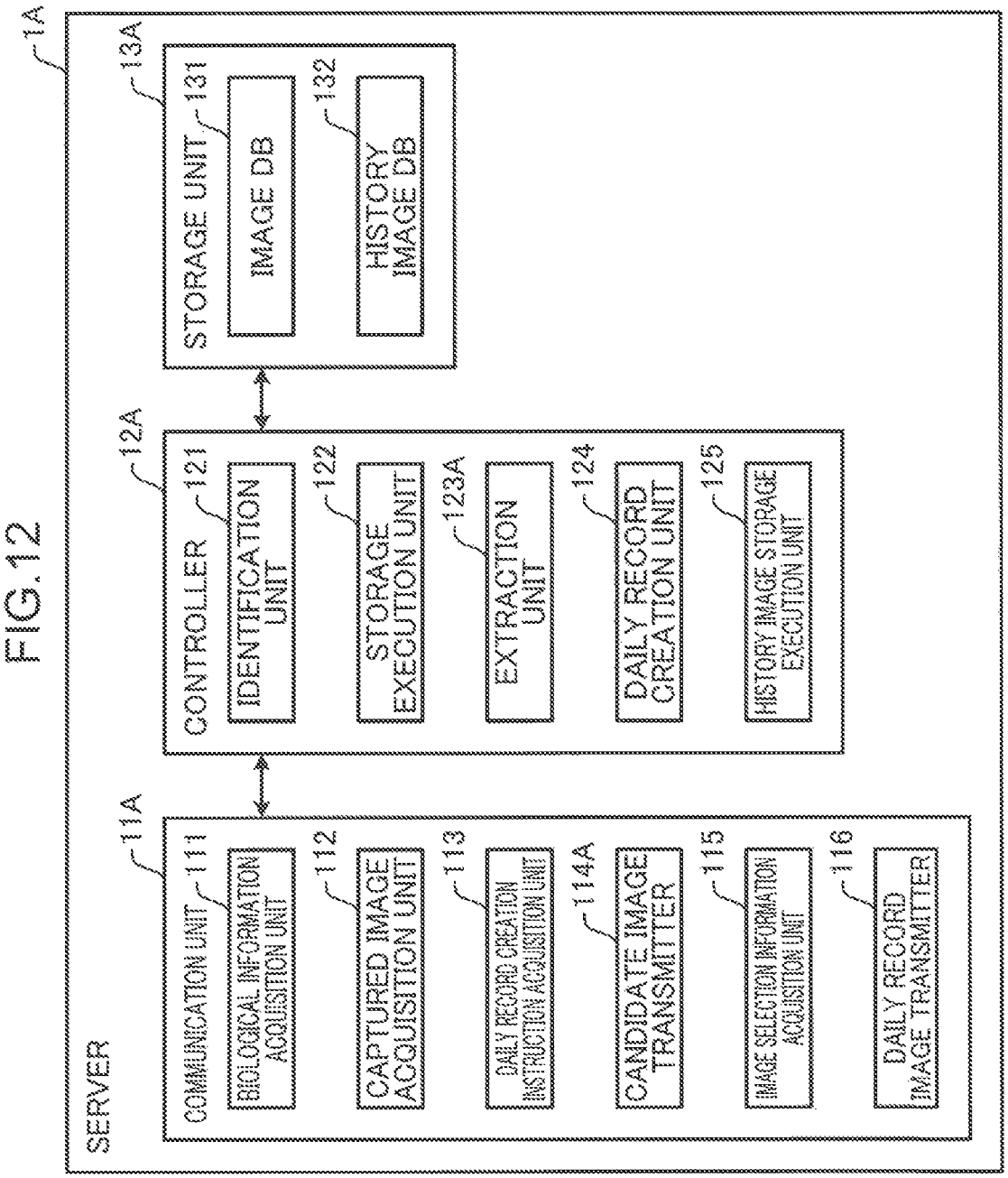
FIG. 12 is a diagram showing a configuration of a server in a second embodiment of the present disclosure.

FIG. 12 is a diagram showing a configuration of a server in the second embodiment of the present disclosure. Note that a configuration of an information processing system in the present second embodiment is the same as the configuration of the information processing system in the first embodiment. In the second embodiment, components identical to components of the first embodiment are denoted with identical reference signs, and descriptions thereof will be omitted. The present second embodiment describes an example in which a nursery-school teacher takes care of a child and creates a daily childcare record for the child in a kindergarten or a nursery school.

The server 1A shown in FIG. 12 includes a communication unit 11A, a controller 12A, and a storage unit 13A.

The communication unit 11A includes a biological information acquisition unit 111, a captured image acquisition unit 112, a daily record creation instruction acquisition unit 113, a candidate image transmitter 114A, an image selection information acquisition unit 115, and a daily record image transmitter 116. The controller 12A is, for example, a CPU, and includes an identification unit 121, a storage execution unit 122, an extraction unit 123A, a daily record creation unit 124, and a history image storage execution unit 125. The storage unit 13A is, for example, a semiconductor memory, and includes an image DB 131 and a history image DB 132.

The history image DB 132 stores a past captured image, a date when the captured image is acquired, and person identification information in association with one another.

The history image storage execution unit 125 stores, in the history image DB 132, the extracted captured image, the date when the captured image is acquired, and the person identification information acquired by the daily record creation instruction acquisition unit 113 in association with one another. In the present second embodiment, from among the captured images extracted by the extraction unit 123A, the history image storage execution unit 125 stores, in the history image DB 132, the captured image selected in a terminal device 4, that is, a candidate image identified by image selection information acquired by the image selection information acquisition unit 115, a date when a daily record image is created using the candidate image, and the acquired person identification information in association with one another. Note that the history image storage execution unit 125 may store the captured image extracted by the extraction unit 123A in the history image DB 132.

The extraction unit 123A extracts, from the image DB 131 of the storage unit 13, the captured image associated with the person identification information acquired by the daily record creation instruction acquisition unit 113 and the biological information corresponding to the state information acquired by the daily record creation instruction acquisition unit 113.

Also, the extraction unit 123A extracts the past candidate image associated with the person identification information acquired by the image selection information acquisition unit 115 from the history image DB 132 as the history image.

The candidate image transmitter 114A transmits the captured image extracted by the extraction unit 123A to the terminal device 4 as the candidate image, and transmits the history image extracted by the extraction unit 123A to the terminal device 4.

Subsequently, an operation of the server 1A in the present second embodiment will be described.

Figure 13:
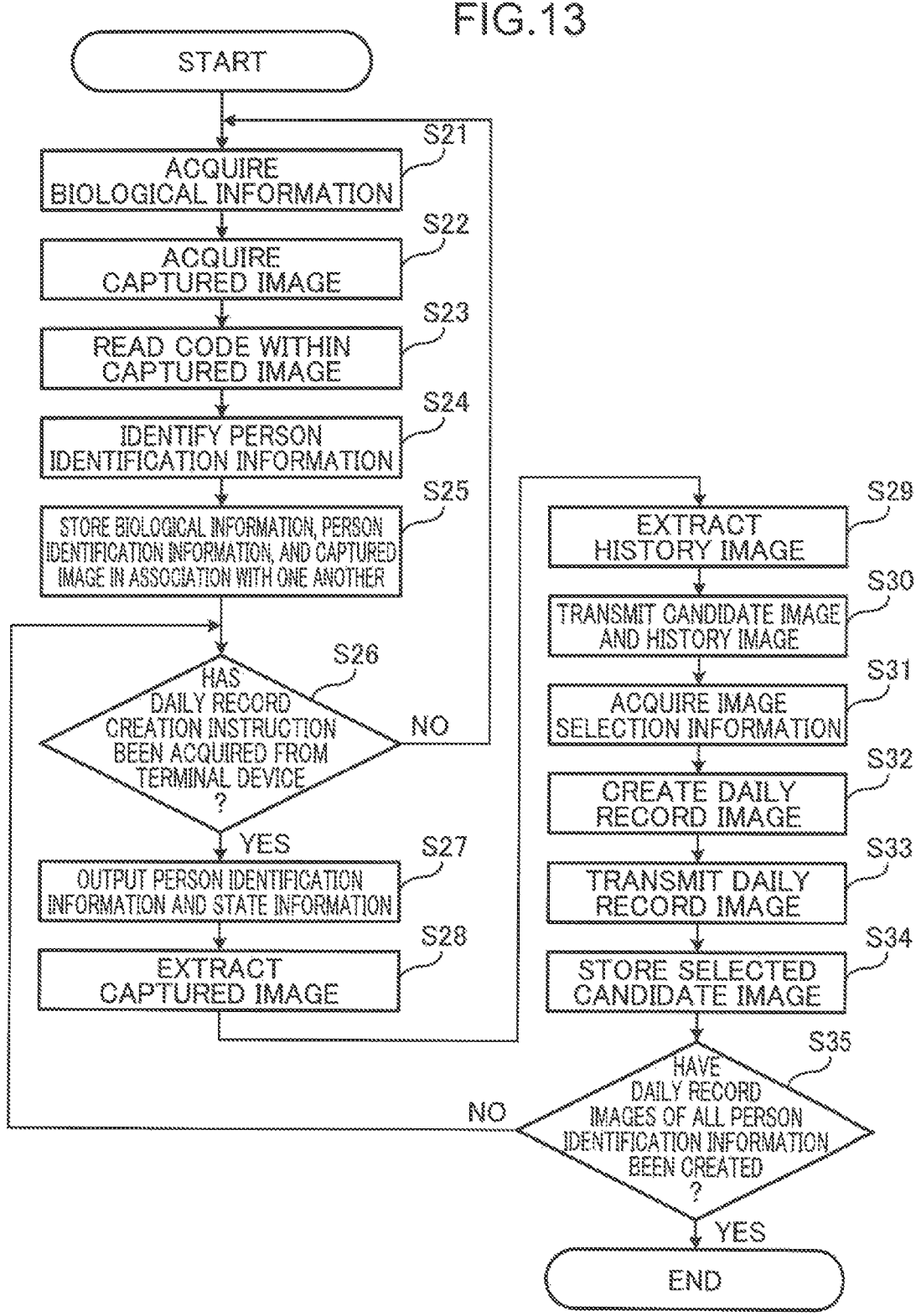
FIG. 13 is a flowchart for describing an operation of the server in the second embodiment of the present disclosure.

FIG. 13 is a flowchart for describing the operation of the server in the second embodiment of the present disclosure.

Note that processing of steps S21 to S26 is the same as processing of steps S1 to S6 shown in FIG. 7, and thus descriptions will be omitted.

When it is determined that the daily record creation instruction is acquired from the terminal device 4 (YES in step S26), in step S27, the daily record creation instruction acquisition unit 113 outputs the person identification information and the state information included in the acquired daily record creation instruction to the extraction unit 123A.

Next, in step S28, the extraction unit 123A extracts, from the image DB 131 of the storage unit 13A, the captured image associated with the person identification information acquired by the daily record creation instruction acquisition unit 113 and the biological information corresponding to the state information acquired by the daily record creation instruction acquisition unit 113. For example, when the acquired state information indicates the state where the degree of excitement is high, the extraction unit 123A extracts the captured image with a heart rate, which is biological information, equal to or greater than a threshold, from among the captured images associated with the acquired person identification information.

Next, in step S29, the extraction unit 123A extracts, from the history image DB 132, the past captured image associated with the person identification information acquired by the image selection information acquisition unit 115 as the history image. Here, the extraction unit 123A extracts, for example, the history images corresponding to a predetermined number of days in the past. The predetermined number of days is three days, for example. The extraction unit 123A extracts, for example, the history image of the previous day, the history image of two days ago, and the history image of three days ago.

Next, in step S30, the candidate image transmitter 114A transmits the captured image extracted by the extraction unit 123A to the terminal device 4 as the candidate image, and transmits the history image extracted by the extraction unit 123A to the terminal device 4. The communication unit 41 of the terminal device 4 receives the candidate image and the history image transmitted by the server 1A. A display unit 44 displays the candidate image and the history image received by the communication unit 41.

Figure 14:
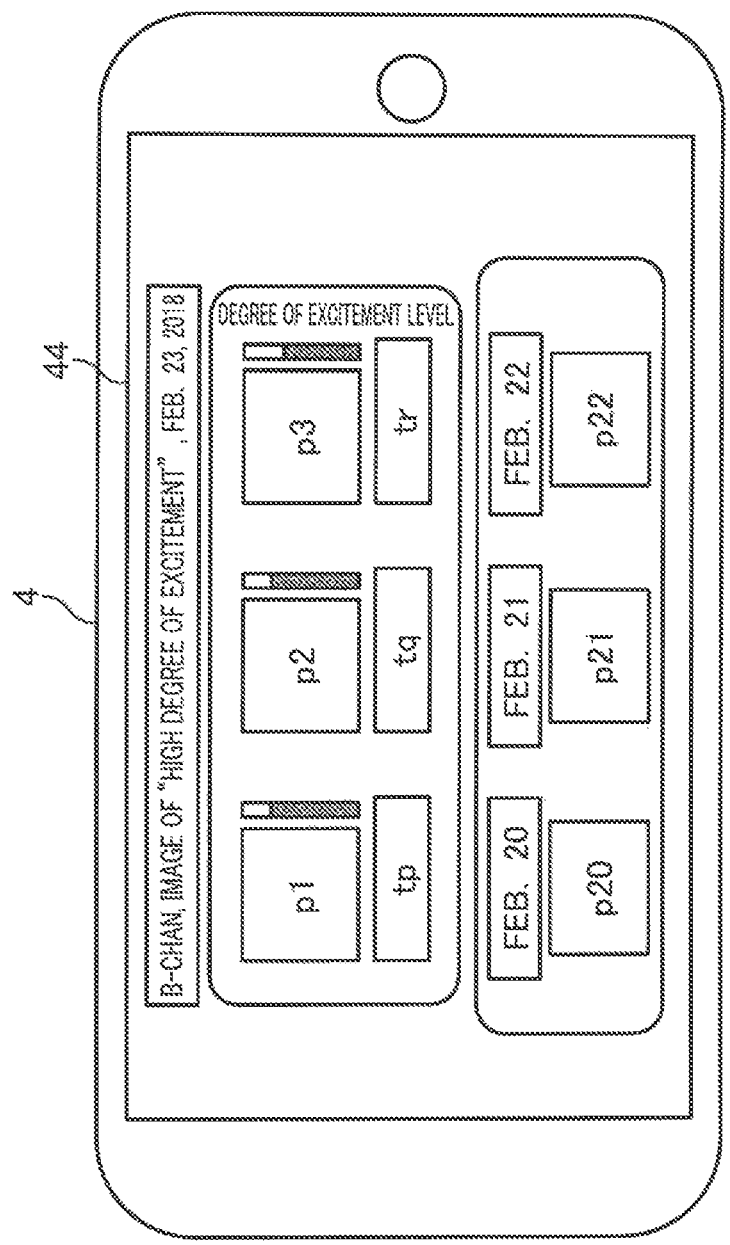
FIG. 14 is a view showing one example of a selection screen that receives selection of a candidate image in a terminal device in the second embodiment of the present disclosure.

FIG. 14 is a view showing one example of a selection screen that receives selection of the candidate image in the terminal device in the second embodiment of the present disclosure.

When the candidate image and the history image transmitted by the server 1A are received, the display unit 44 of the terminal device 4 displays the selection screen shown in FIG. 14. The selection screen shown in FIG. 14 includes a name of a child, a state of the child, today's date, at least one candidate image, time when each candidate image is acquired, excitement degree level indicating to what degree the child is excited, and at least one history image.

In FIG. 14, the name of the child "B-chan", the state of the child indicating that the degree of excitement is high, the date "Feb. 23, 2018", the candidate images p1, p2, and p3, the time tp, tq, and tr, and the excitement degree level are displayed. The excitement degree level is displayed according to magnitude of the heart rate. In addition, in FIG. 14, the history images p20, p21, and p22, and "February 20", "February 21", and "February 22" which are dates when the history images p20, p21, and p22 are captured are displayed, respectively. These pieces of information are received from the server 1A together with the candidate images. That is, the candidate image transmitter 114A transmits, to the terminal device 4, the name of the child corresponding to the person identification information, the state information, today's date, at least one candidate image, the time associated with each candidate image, the biological information associated with each candidate image, and at least one history image. The communication unit 41 of the terminal device 4 receives these pieces of information transmitted by the server 1A.

The nursery-school teacher selects the candidate image to be put on the daily record by tapping the desired candidate image among the plurality of candidate images p1, p2, and p3 displayed on the selection screen. At this time, by checking the history images p20, p21, and p22, the nursery-school teacher can select the desired candidate image so as to avoid overlapping past images. The input reception unit 43 receives a selection operation of the nursery-school teacher on the candidate image. When the candidate image is tapped by the nursery-school teacher, the communication unit 41 transmits the image selection information indicating the selected candidate image to the server 1A. Note that the image selection information may be the selected candidate image, or may be information for identifying the selected candidate image.

Returning to FIG. 13, processing of steps S31 to S33 is the same as processing of steps S10 to S12 shown in FIG. 7, and thus descriptions will be omitted.

Next, in step S34, the history image storage execution unit 125 stores, in the history image DB 132, the candidate image selected by the nursery-school teacher and shown by the acquired image selection information, the date when the daily record image is created using the candidate image, and the person identification information acquired by the daily record creation instruction acquisition unit 113 in association with one another.

Processing of step S35 is the same as processing of step S13 shown in FIG. 7, and thus descriptions will be omitted.

In this way, in the present second embodiment, the extracted captured image is transmitted to the terminal device 4 as the candidate image, and the extracted history image is transmitted to the terminal device 4, the history image selected in the past together with the candidate image to be put on the daily record are presented to the nursery-school teacher. Therefore, by checking the history image, the nursery-school teacher can select the desired candidate image so as to prevent overlapping past images. As a result, creation of the daily record by the nursery-school teacher can be supported.

Third Embodiment

The first embodiment presents captured images extracted based on biological information to the terminal device. The third embodiment presents, to the terminal device, information on a playing tool that attracts interest of a child when the captured image is captured together with the captured image extracted based on the biological information.

Figure 15:
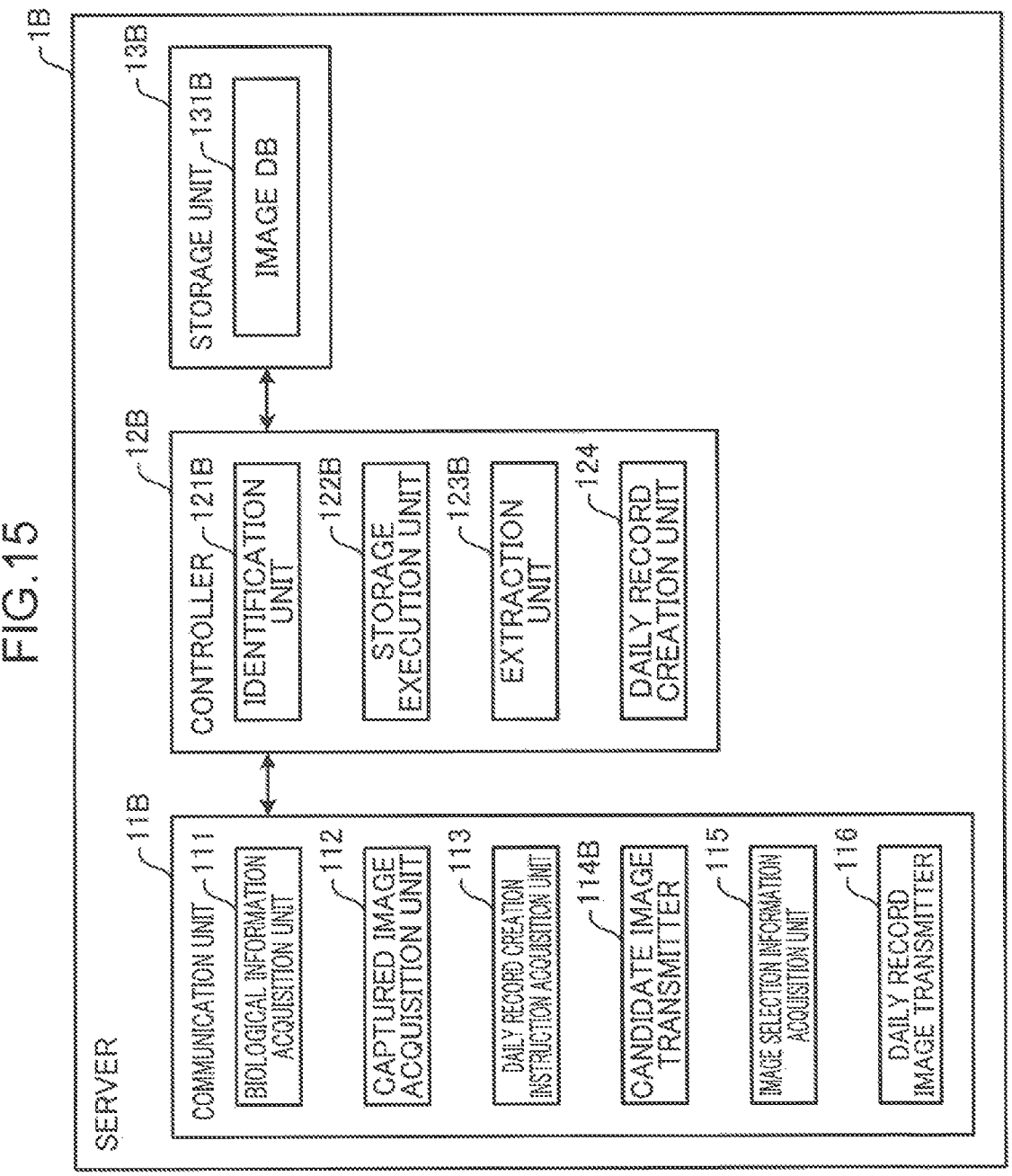
FIG. 15 is a diagram showing a configuration of a server in a third embodiment of the present disclosure.

FIG. 15 is a diagram showing a configuration of a server in the third embodiment of the present disclosure. Note that a configuration of an information processing system in the present third embodiment is the same as the configuration of the information processing system in the first embodiment. In the third embodiment, components identical to components of the first embodiment are denoted with identical reference signs, and descriptions thereof will be omitted. The present third embodiment describes an example in which a nursery-school teacher takes care of a child and creates a daily childcare record for the child in a kindergarten or a nursery school.

The server 1B shown in FIG. 15 includes a communication unit 11B, a controller 12B, and a storage unit 13B.

The communication unit 11B includes a biological information acquisition unit 111, a captured image acquisition unit 112, a daily record creation instruction acquisition unit 113, a candidate image transmitter 114B, an image selection information acquisition unit 115, and a daily record image transmitter 116. The controller 12B is, for example, a CPU, and includes an identification unit 121B, a storage execution unit 122B, an extraction unit 123B, and a daily record creation unit 124. The storage unit 13B is, for example, a semiconductor memory, and includes an image DB 131B.

Based on the captured image acquired by the captured image acquisition unit 112, the identification unit 121B identifies person identification information for identifying the child. By authenticating a face of the child within the captured image acquired by the captured image acquisition unit 112, the identification unit 121B identifies the person identification information included in the captured image. In this case, the storage unit 13B stores in advance the face image of the child and the person identification information in association with each other. Also, the identification unit 121B further identifies a position of the child (first person) within the captured image. For example, within the captured image, the identification unit 121B identifies position coordinates where the authenticated face of the child exists as the position of the child within the captured image.

Based on the captured image acquired by the captured image acquisition unit 112, the identification unit 121B identifies playing tool identification information for identifying the playing tool. The playing tool is, for example, building blocks, a picture book, or a swing, and exists within the same space as the child does. A code having the playing tool identification information is attached to a surface of the playing tool. By reading the code in the captured image, the identification unit 121B identifies the playing tool identification information included in the captured image. Also, the identification unit 121B further identifies a position of the playing tool within the captured image. For example, within the captured image, the identification unit 121B identifies the position coordinates where the read playing tool exists as the position of the playing tool within the captured image. The identification unit 121B further identifies the position of the playing tool within the past captured image acquired before the acquired current captured image in terms of time.

Note that as the code, for example, Colorbit described above is used. Colorbit is consecutive arrangement of cells of a plurality of colors, and is generated by converting the playing tool identification information based on a predetermined standard. By decoding Colorbit within the captured image, the identification unit 121B obtains the playing tool identification information. Colorbit has characteristics of being able to identify positions of Colorbit codes within the captured image, and to read a plurality of Colorbit codes within the captured image collectively. Therefore, by reading the plurality of Colorbit codes within the captured image, the identification unit 121B can identify the playing tool identification information and the positional information on a plurality of playing tools.

In the present third embodiment, the identification unit 121B identifies the person identification information included in the captured image by authenticating the face of the child within the captured image. However, the present disclosure is not particularly limited to this example. The code having the person identification information may be attached to the surface of the person in a similar manner to the playing tool identification information, and the identification unit 121B may identify the person identification information included in the captured image by reading the code within the captured image.

Furthermore, in the present third embodiment, the identification unit 121B identifies the playing tool identification information by reading the code within the captured image. However, the present disclosure is not particularly limited to this example, and the identification unit 121B may identify the playing tool identification information by authenticating an image of the playing tool within the captured image. In this case, the storage unit 13B stores in advance the playing tool image and the playing tool identification information in association with each other.

The storage execution unit 122B stores, in the image DB 131B of the storage unit 13B, the person identification information identified by the identification unit 121B, the biological information acquired by the biological information acquisition unit 111, the captured image acquired by the captured image acquisition unit 112, and the playing tool identification information identified by the identification unit 121B in association with one another.

FIG. 16 is a diagram showing one example of data structure of the image DB in the third embodiment of the present disclosure. "Child ID-1" of FIG. 16 shows the person identification information on a specified child.

The image DB 131B stores the captured image, the biological information, time, and the playing tool identification information for each piece of person identification information in association with one another. The captured image represents a file name in which the captured image is stored, and the time represents time when the captured image and the biological information are acquired in the server 1B. Note that the time may be time when a camera 2 and biological information measurement devices 3 transmit the captured image and the biological information to the server 1B. The biological information is, for example, numerical values such as a heart rate. The playing tool identification information represents the playing tool identification information identified by the identification unit 121B.

The storage execution unit 122B stores, in the image DB 131B, the playing tool identification information on the playing tool with a distance between the position of the child (first person) and the position of the playing tool shorter than a predetermined threshold and the position moving, the person identification information, the biological information, and the captured image in association with one another.

Here, it is necessary to identify with which playing tool the child is playing with interest. Therefore, the storage execution unit 122B estimates the playing tool with the distance between the position of the child within the captured image and the position of the playing tool within the captured image shorter than a predetermined threshold and the position moving, as the playing tool with which the child is playing with interest. It is determined whether the position of the playing tool is moving by comparing the position of the playing tool within the current captured image with the position of the playing tool within the past captured image acquired before the current captured image in terms of time. Note that the storage execution unit 122B may estimate the playing tool with the distance between the position of the child within the captured image and the position of the playing tool within the captured image being the shortest and the position moving, as the playing tool with which the child is playing with interest. In this way, the playing tool that exists near the child with the position moving is estimated as the playing tool with which the child is playing with interest.

Also, the storage execution unit 122B may estimate the playing tool with the distance between the position of the child within the captured image and the position of the playing tool within the captured image shorter than a predetermined threshold, as the playing tool with which the child is playing with interest. Note that the storage execution unit 122B may estimate the playing tool with the distance between the position of the child within the captured image and the position of the playing tool within the captured image being the shortest, as the playing tool with which the child is playing with interest. In this way, the playing tool that just exists near the child may be estimated as the playing tool with which the child is playing with interest.

Furthermore, when only one piece of playing tool identification information is identified by the identification unit 121B, it is possible to estimate that the child is playing using the playing tool shown by the playing tool identification information. Therefore, when only one piece of playing tool identification information is identified by the identification unit 121B, the storage execution unit 122B may store, in the image DB 131B, one piece of identified playing tool identification information, the person identification information, the biological information, and the captured image in association with one another.

The extraction unit 123B extracts, from the image DB 131B of the storage unit 13B, the captured image and the playing tool identification information associated with the person identification information acquired by the daily record creation instruction acquisition unit 113 and the biological information corresponding to the state information acquired by the daily record creation instruction acquisition unit 113.

The candidate image transmitter 114B transmits the captured image extracted by the extraction unit 123B to the terminal device 4 as the candidate image, and transmits the playing tool identification information extracted together with the captured image to the terminal device 4.

Subsequently, an operation of the server 1B in the present third embodiment will be described.

Figure 17:
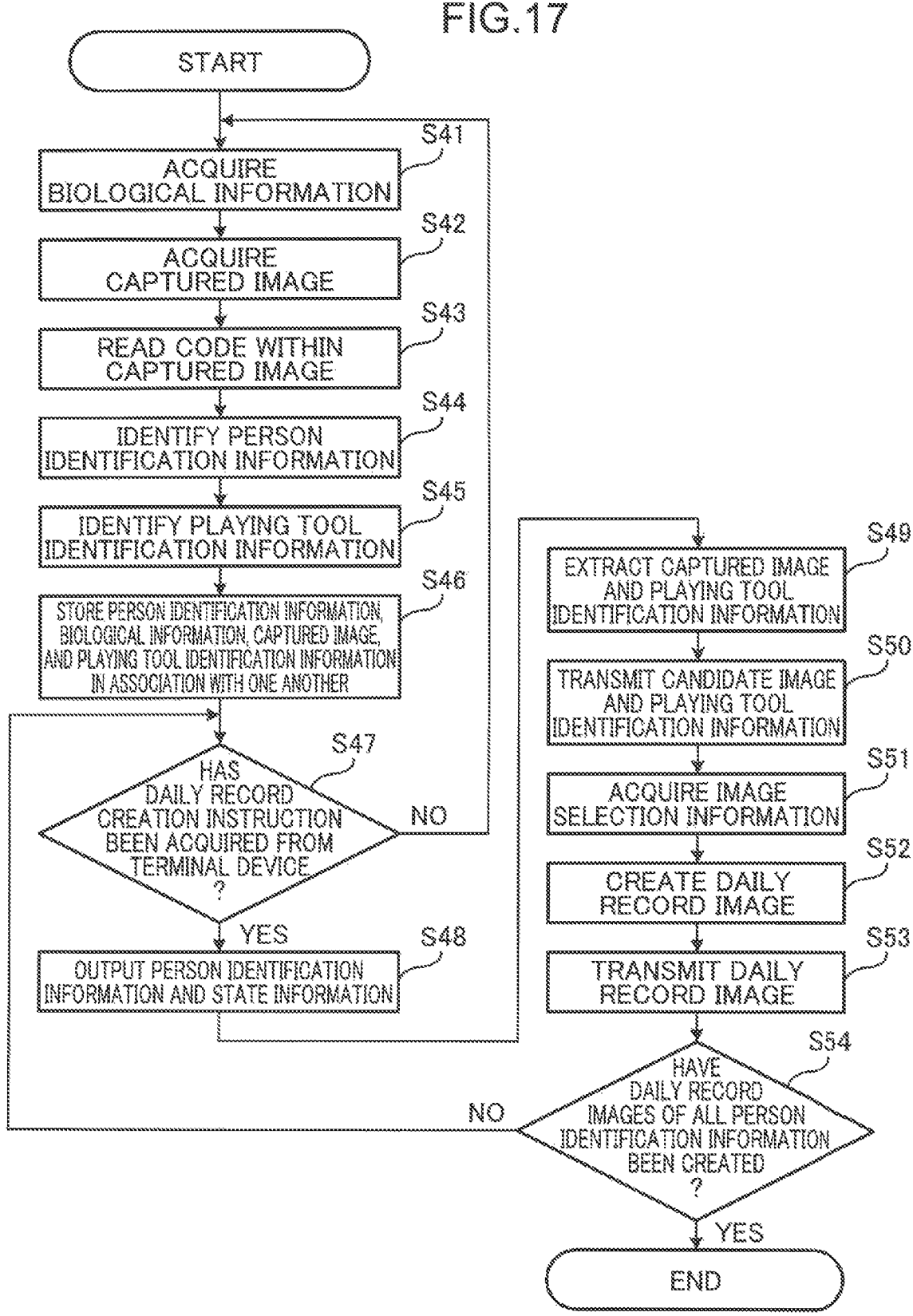
FIG. 17 is a flowchart for describing an operation of the server in the third embodiment of the present disclosure.

FIG. 17 is a flowchart for describing the operation of the server in the third embodiment of the present disclosure.

Note that processing of steps S41 to S44 is the same as processing of steps S1 to S4 shown in FIG. 7, and thus descriptions will be omitted.

Next, in step S45, the identification unit 121B identifies the playing tool identification information included in the captured image.

Next, in step S46, the storage execution unit 122B stores, in the image DB 131B of the storage unit 13B, the biological information acquired by the biological information acquisition unit 111, the person identification information identified by the identification unit 121B, the captured image acquired by the captured image acquisition unit 112, and the playing tool identification information identified by the identification unit 121B, in association with one another. At this time, the storage execution unit 122B stores, in the image DB 1318, the playing tool identification information on the playing tool with a distance between the position of the child and the position of the playing tool shorter than a predetermined threshold and the position moving, the person identification information, the biological information, and the captured image in association with one another.

Processing of steps S47 to S48 is the same as processing of steps S6 to S7 shown in FIG. 7, and thus descriptions will be omitted.

Next, in step S49, the extraction unit 123B extracts, from the image DB 131B of the storage unit 138, the captured image and the playing tool identification information associated with the person identification information acquired by the daily record creation instruction acquisition unit 113 and the biological information corresponding to the state information acquired by the daily record creation instruction acquisition unit 113. For example, when the acquired state information indicates the state where the degree of excitement is high, the extraction unit 123B extracts the captured image and the playing tool identification information with a heart rate, which is biological information, equal to or greater than a threshold, from among the captured images and the playing tool identification information associated with the acquired person identification information.

Next, in step S50, the candidate image transmitter 114B transmits the captured image extracted by the extraction unit 123B to the terminal device 4 as the candidate image, and transmits the playing tool identification information extracted by the extraction unit 123B to the terminal device 4. The communication unit 41 of the terminal device 4 receives the candidate image and the playing tool identification information transmitted by the server 1B. A display unit 44 displays the candidate image and the playing tool identification information received by the communication unit 41.

Figure 18:
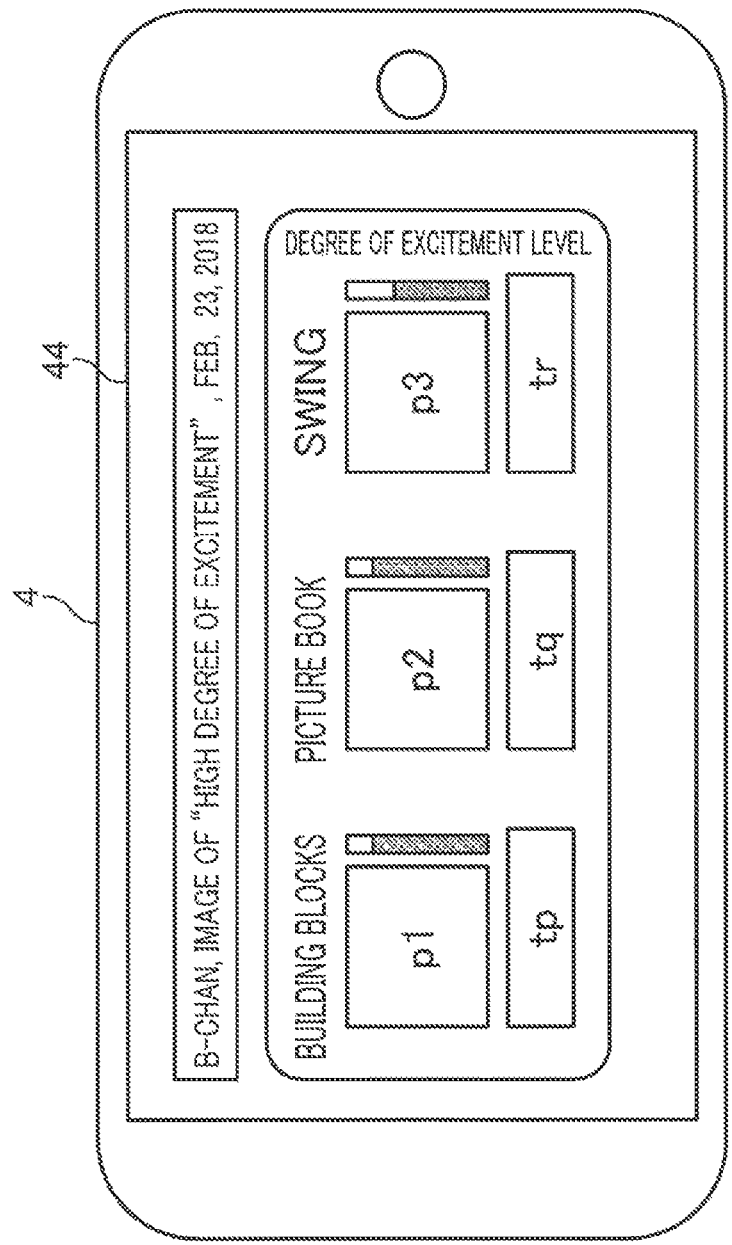
FIG. 18 is a view showing one example of a selection screen that receives selection of a candidate image in a terminal device in the third embodiment of the present disclosure.

FIG. 18 is a view showing one example of a selection screen that receives selection of the candidate image in the terminal device in the third embodiment of the present disclosure.

When the candidate image and the playing tool identification information transmitted by the server 1B are received, the display unit 44 of the terminal device 4 displays the selection screen shown in FIG. 18. The selection screen shown in FIG. 18 includes a name of a child, a state of the child, today's date, at least one candidate image, time when each candidate image is acquired, excitement degree level indicating to what degree the child is excited, and the playing tool identification information indicating the playing tool the child is using within each candidate image.

In FIG. 18, the name of the child "B-chan", the state of the child indicating that the degree of excitement is high, the date "Feb. 23, 2018", the candidate images p1, p2, and p3, the time tp, tq, and tr, and the excitement degree level are displayed. The excitement degree level is displayed according to magnitude of the heart rate. In FIG. 18, the playing tool identification information "building blocks", "picture book", and "swing" is displayed above the candidate images p1, p2, and p3, respectively. These pieces of information are received from the server 1B together with the candidate images. That is, the candidate image transmitter 114B transmits, to the terminal device 4, the name of the child corresponding to the person identification information, the state information, today's date, at least one candidate image, the time associated with each candidate image, the biological information associated with each candidate image, and the playing tool identification information associated with each candidate image. The communication unit 41 of the terminal device 4 receives these pieces of information transmitted by the server 1B.

The nursery-school teacher selects the candidate image to be put on the daily record by tapping the desired candidate image among the plurality of candidate images p1, p2, and p3 displayed on the selection screen. At this time, with the displayed playing tool identification information, the nursery-school teacher can select the desired candidate image while confirming what kind of playing tool attracts interest of the child. The input reception unit 43 receives a selection operation of the nursery-school teacher on the candidate image. When the candidate image is tapped by the nursery-school teacher, the communication unit 41 transmits the image selection information indicating the selected candidate image to the server 1B. Note that the image selection information may be the selected candidate image, or may be information for identifying the selected candidate image.

Returning to FIG. 17, processing of steps S51 to S54 is the same as processing of steps S10 to S13 shown in FIG. 7, and thus descriptions will be omitted.

In this way, in the present third embodiment, the extracted captured image is transmitted to the terminal device 4 as the candidate image, and the extracted playing tool identification information is transmitted to the terminal device 4. Then, the nursery-school teacher is presented with the playing tool identification information together with the candidate image to be put on the daily record. Therefore, the nursery-school teacher can select the desired candidate image while checking the playing tool that attracts interest of the child. As a result, creation of the daily record by the nursery-school teacher can be supported.

The above-described second embodiment may be combined with the present third embodiment. That is, in the present third embodiment, the extracted captured image may be transmitted to the terminal device 4 as the candidate image, and the extracted history image and the playing tool identification information may be transmitted to the terminal device 4. Then, the nursery-school teacher may be presented with the history image and the playing tool identification information selected in the past, together with the candidate image to be put on the daily record.

The present first to third embodiments describe examples in which the first person is a child, the second person is a nursery-school teacher, the nursery-school teacher takes care of the child in a kindergarten or a nursery school, and the daily childcare record for the child is created. However, the present disclosure is not particularly limited to these examples, and can be applied to an example in which the first person is a person who receives nursing care, such as a senior citizen, the second person is a care worker, and the care worker cares for the person who needs nursing care in a welfare facility such as a day service center or a home for the aged, and a daily care record for the person who needs nursing care is created.

As described above, the device of the present disclosure has been described based on the embodiments, but the present disclosure is not limited to these embodiments. The present embodiments to which various modifications conceivable by a person skilled in the art are made and embodiments that are made by combining components of different embodiments may also be within the scope of one or more aspects of the present disclosure as long as such embodiments do not depart from the spirit of the present disclosure.

In each of the embodiments described above, each component may be implemented with dedicated hardware or by executing a software program suitable for the component. Each component may be implemented by a program execution unit such as a CPU or a processor reading and executing a software program recorded on a recording medium, such as a hard disk or a semiconductor memory.

Part or all of functions of the device according to the embodiments of the present disclosure are typically implemented as a large scale integration (LSI), which is an integrated circuit. These functions may be formed as separate chips, or some or all of the functions may be included in one chip. The circuit integration is not limited to LSI, and may be implemented using a dedicated circuit or a general-purpose processor. A field programmable gate array (FPGA) that is programmable after manufacturing of an LSI or a reconfigurable processor in which connections and settings of circuit cells within the LSI are reconfigurable may be used.

Part or all of functions of the device according to the embodiments of the present disclosure may be implemented by a processor such as a CPU executing a program.

Numerical values used above are merely illustrative to be used to specifically describe the present disclosure, and thus the present disclosure is not limited to the illustrative numerical values.

Order in which steps shown in the flowcharts are executed is merely illustrative to be used to specifically describe the present disclosure, and thus steps may be executed in order other than the above order as long as similar effects are obtained. Some of the steps may be executed simultaneously (in parallel) with other steps.

Furthermore, various modifications in which changes conceivable by a person skilled in the art are made to the embodiments of the present disclosure may also be within the scope of the present disclosure as long as such modifications do not depart from the spirit of the present disclosure.

The information processing method, the information processing device, and the information processing system according to the present disclosure can identify behavior in which the first person is interested, and provide an image indicating the state of the first person when the first person is performing the behavior in which the first person is interested, and are useful as the information processing method, the information processing device, and the information processing system that extract predetermined images.

This application is based on Japanese Patent application No. 2018-071841 filed in Japan Patent Office on Apr. 3, 2018, the contents of which are hereby incorporated by reference.

Although the present invention has been fully described by way of example with reference to the accompanying drawings, it is to be understood that various changes and modifications will be apparent to those skilled in the art. Therefore, unless otherwise such changes and modifications depart from the scope of the present invention hereinafter defined, they should be construed as being included therein.

The invention claimed is:

1. An information processing method comprising, by a computer:
   acquiring biological information on a first person;
   acquiring an image obtained by imaging the first person in synchronization with acquisition timing of the biological information;
   identifying person identification information for identifying the first person based on the image;
   storing, in a storage, the identified person identification information, the acquired biological information, and the acquired image in association with one another;
   displaying a display screen that prompts a second person to select the person identification information and state information as search keys, the second person being different from the first person, the state information indicating a state of the first person;
   receiving, via the display screen, the person identification information selected by the second person and the state information selected by the second person;
   searching the storage using the selected person identification information and the selected state information as search keys, to extract the image associated with the person identification information selected by the second person and the biological information corresponding to the state information selected by the second person; and
   displaying the image extracted from the storage.

2. The information processing method according to claim 1, wherein the state information includes psychological state information indicating a psychological state of the first person.

3. The information processing method according to claim 1, further comprising transmitting the extracted image to a terminal device the second person uses.

4. The information processing method according to claim 1, further comprising:
   storing, in the storage, the extracted image, a date when the image is acquired, and the acquired person identification information in association with one another; and
   extracting, from the storage, a past image associated with the acquired person identification information as a history image.

5. The information processing method according to claim 4, further comprising transmitting the extracted history image together with the extracted image to a terminal device the second person uses.

6. The information processing method according to claim 1, wherein
   a code having the person identification information is attached to a surface of the first person, and
   identifying the person identification information includes identifying the person identification information by reading the code within the image.

7. The information processing method according to claim 1, wherein identifying the person identification information includes identifying the person identification information by authenticating a face of the first person within the image.

8. The information processing method according to claim 1, further comprising identifying playing tool identification information for identifying a playing tool based on the image, wherein
   the storing includes storing, in the storage, the person identification information, the biological information, the image, and the playing tool identification information in association with one another, and
   the searching includes searching the storage, for the image and the playing tool identification information associated with the acquired person identification information selected by the second person and the biological information corresponding to the state information selected by the second person.

9. The information processing method according to claim 8, wherein
   a code having the playing tool identification information is attached to a surface of the playing tool, and
   identifying the playing tool identification information includes identifying the playing tool identification information by reading the code within the image.

10. The information processing method according to claim 8, wherein
    identifying the person identification information includes further identifying a position of the first person within the image,
    identifying the playing tool identification information includes further identifying a position of the playing tool within the image, and further identifying a position of the playing tool within a past image acquired before the acquired image in terms of time, and
    the storing includes storing, in the storage, the playing tool identification information on the playing tool with a distance between the position of the first person and the position of the playing tool within the image shorter than a predetermined threshold and the position moving, the person identification information, the biological information, and the image in association with one another.

11. The information processing method according to claim 8, wherein
    identifying the person identification information includes further identifying a position of the first person within the image,
    identifying the playing tool identification information includes further identifying a position of the playing tool within the image, and
    the storing includes storing, in the storage, the playing tool identification information on the playing tool with a distance between the position of the first person and the position of the playing tool shorter than a predetermined threshold, the person identification information, the biological information, and the image in association with one another.

12. An information processing device comprising:
    a communication unit;
    a processor; and
    a memory,
    wherein the communication unit acquires biological information on a first person, the communication unit acquires an image obtained by imaging the first person in synchronization with acquisition timing of the biological information, the processor identifies person identification information for identifying the first person based on the image, the processor stores, in the memory, the identified person identification information, the acquired biological information, and the acquired image in association with one another, the processor displays, on a display, a display screen that prompts a second person to select the person identification information and state information as search keys, the second person being different from the first person, the state information indicating a state of the first person, the communication unit receives, via the display screen, the person identification information selected by the second person and state information selected by the second person, the processor searches the memory using the selected person identification information and the selected state information as search keys, to extract the image associated with the person identification information selected by the second person and the biological information corresponding to the state information selected by the second person, and the processor displays, on the display, the image extracted from the memory.

13. An information processing system comprising:

a camera;
a biological information measurement device;
an information processing device; and
a terminal device, wherein
the camera includes:
  an imaging device that images a first person; and
  a transmitter that transmits an image captured by the imaging device to the information processing device,
the biological information measurement device includes:
  a sensor that measures biological information on the first person; and
  a transmitter that transmits the biological information measured by the sensor to the information processing device,
the terminal device includes:
  a display that displays a display screen that prompts a second person to select person identification information identifying the first person and state information as search keys, the second person being different from the first person, the state information indicating a state of the first person,
  a processor that receives, via the display screen, an input by the second person to select the person identification information and the state information, and
  a transmitter that transmits the person identification information and the state information selected by the second person,
the information processing device includes:
  a storage;
  a processor that performs operations including:
    acquiring the biological information transmitted by the biological information measurement device;
    acquiring the image transmitted by the camera in synchronization with acquisition timing of the biological information;
    identifying the person identification information for identifying the first person based on the image;
    storing, in the storage, the identified person identification information, the acquired biological information, and the acquired image in association with one another;
    receiving, from the terminal device, the person identification information selected by the second person and the state information selected by the second person;
    searching the storage, using the selected person identification information and the selected state information as search keys, to extract the image associated with the person identification information selected by the second person and the biological information corresponding to the state information selected by the second person; and
  a transmitter that transmits the extracted image to the terminal device,
the terminal device further includes:
  a receiver that receives the image transmitted by the information processing device, and
  the display displays the image received by the receiver.

* * * * *